United States Patent
Wiebe, III

(10) Patent No.: US 8,419,760 B2
(45) Date of Patent: Apr. 16, 2013

(54) CUTTING ACCESSORY FOR A POWERED SURGICAL HANDPIECE, THE CUTTING ACCESSORY INCLUDING FEATURES TO FACILITATE THE ALIGNMENT OF THE ACCESSORY WITH THE HANDPIECE, HOLD THE ACCESSORY TO THE HANDPIECE, FACILITATE THE TRANSFER OF TORQUE TO THE ACCESSORY AND REDUCE THE WOBBLE OF THE ACCESSORY

(75) Inventor: James B. Wiebe, III, Riner, VA (US)

(73) Assignee: Stryker Corporation, Kalamazoo, MI (US)

( * ) Notice: Subject to any disclaimer, the term of this patent is extended or adjusted under 35 U.S.C. 154(b) by 1683 days.

(21) Appl. No.: 11/471,266

(22) Filed: Jun. 20, 2006

(65) Prior Publication Data
US 2007/0021766 A1 Jan. 25, 2007

Related U.S. Application Data

(60) Provisional application No. 60/693,638, filed on Jun. 25, 2005.

(51) Int. Cl.
*A61B 17/32* (2006.01)
*B23B 31/02* (2006.01)
*B23B 31/06* (2006.01)
*B25B 23/00* (2006.01)

(52) U.S. Cl.
USPC .............................. 606/180; 279/145; 81/438

(58) Field of Classification Search .............. 606/79–81, 606/180, 167, 170, 1, 108; 279/22, 24, 143, 279/145, 76, 904, 906, 902, 62, 140, 147, 279/82, 155, 901; 81/3.07, 438; 285/345, 285/332, 35, 256, 29, 26, 33; 408/226, 239, 408/97; 604/905, 536, 535
See application file for complete search history.

(56) References Cited

U.S. PATENT DOCUMENTS

| 4,641,551 | A | 2/1987 | Pascaloff |
| 5,207,697 | A | 5/1993 | Carusillo et al. |
| 5,782,836 | A | 7/1998 | Umber |
| 5,975,900 | A | 11/1999 | Garman |
| 5,993,454 | A | 11/1999 | Longo |
| 6,139,228 | A * | 10/2000 | Longo ........................... 606/180 |
| 6,755,424 | B1 * | 6/2004 | Paulsen ......................... 279/145 |
| 6,929,266 | B2 * | 8/2005 | Peters et al. .................... 279/82 |
| 6,958,071 | B2 * | 10/2005 | Carusillo et al. .............. 606/180 |
| 2006/0053974 | A1 | 3/2006 | Blust et al. |

FOREIGN PATENT DOCUMENTS

| DE | 103 11 455 B3 | 9/2004 |
| JP | 57-139330 A | 8/1982 |
| JP | 2002-523174 A | 7/2002 |
| WO | 02/076308 A2 | 10/2002 |
| WO | WO 02/076308 A2 | 10/2002 |
| WO | WO 2004/006787 A2 | 1/2004 |

OTHER PUBLICATIONS

Stryker ¼ Inch Chuck, Part No. 0277-084-138, Jan. 2000, 2 Sheets.
PCT App. No. PCT/US2006/024200, International Search Report, Oct. 2006.
PCT App. No. PCT/US2006/02400, Written Opinion of ISA, Oct. 2006.

* cited by examiner

*Primary Examiner* — Kathleen Holwerda
*Assistant Examiner* — Jocelin Tanner

(57) ABSTRACT

A surgical handpiece with a rotating spindle for receiving the coupling head of a surgical attachment or a cutting accessory. A gear train has plural drive heads that simultaneously rotate at different speeds. A clutch assembly has pins that move along the length of the spindle. The clutch assembly sets the position of the pins so they will engage one of the drive heads. The spindle rotates with the drive head with which the clutch pins are engaged.

20 Claims, 20 Drawing Sheets

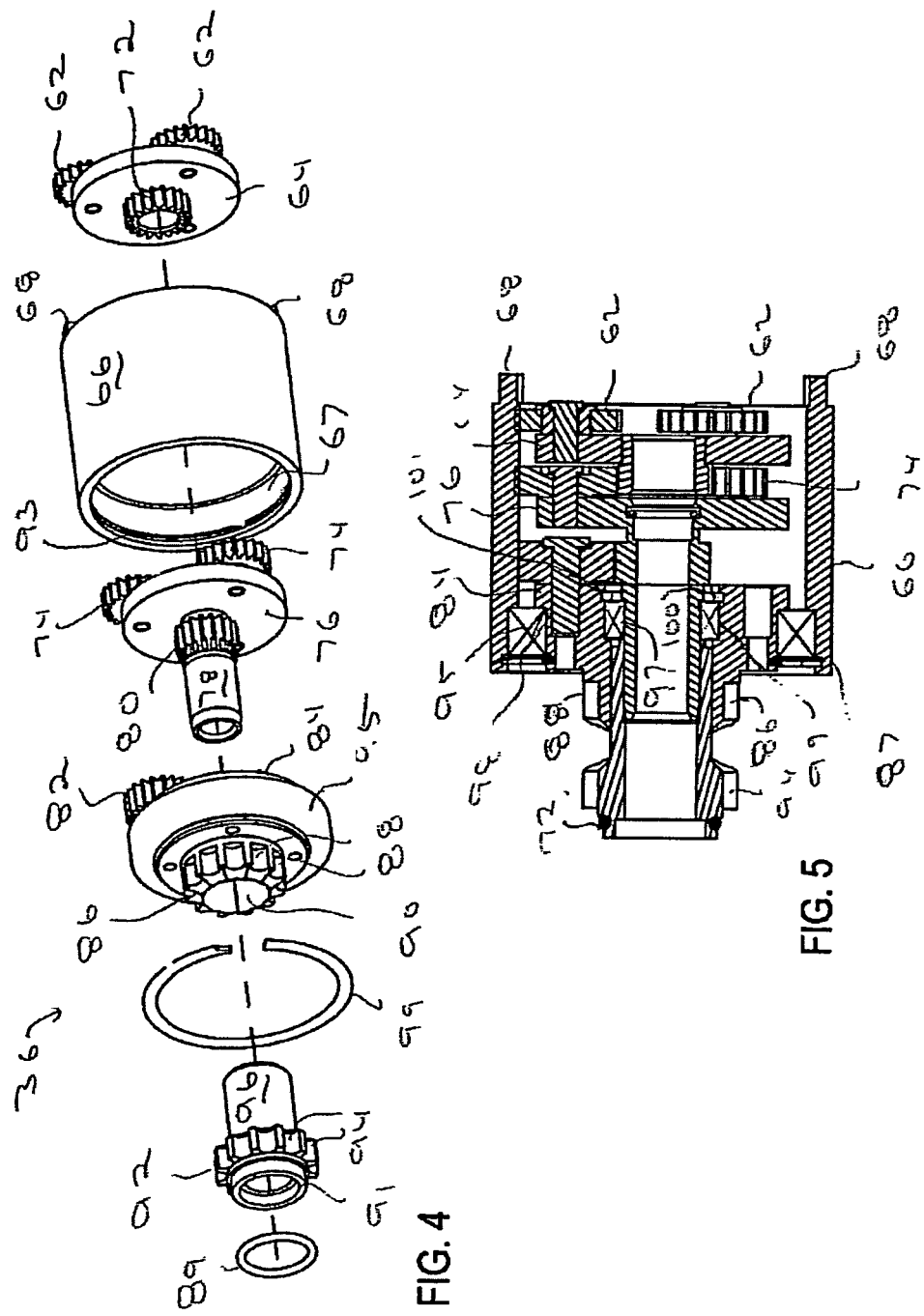

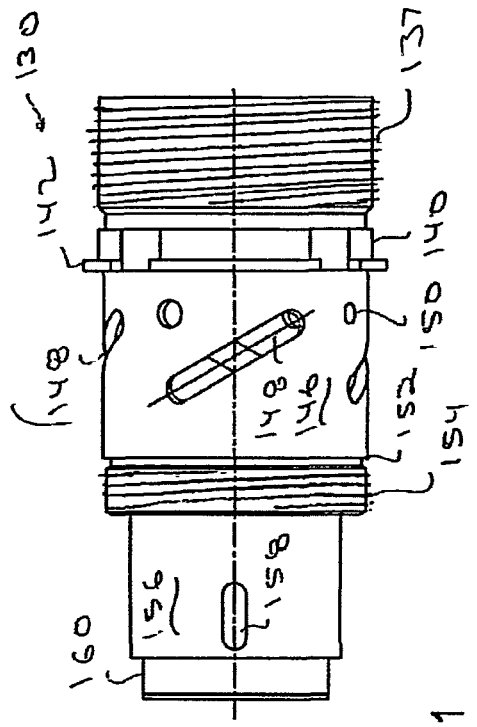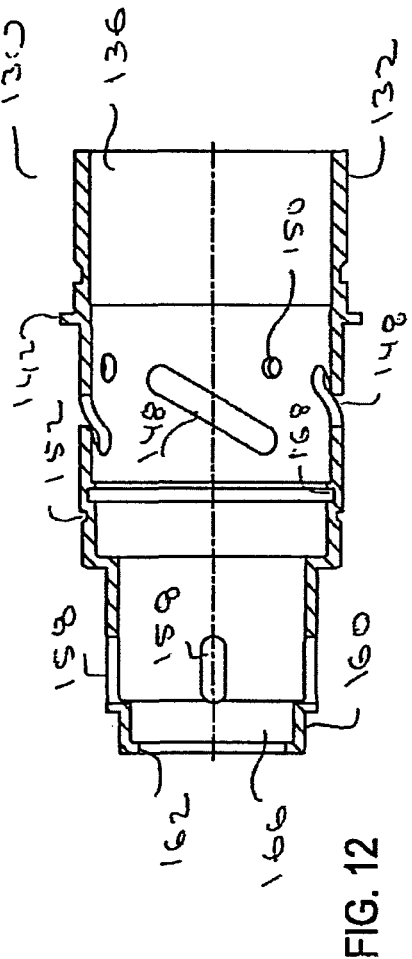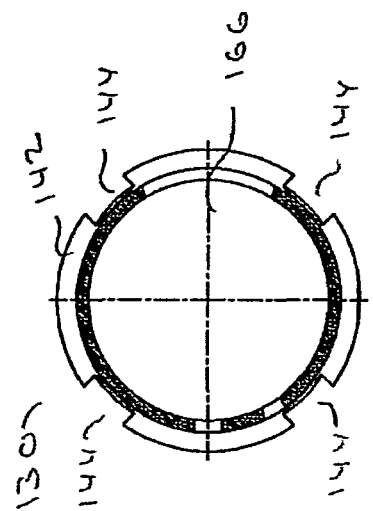

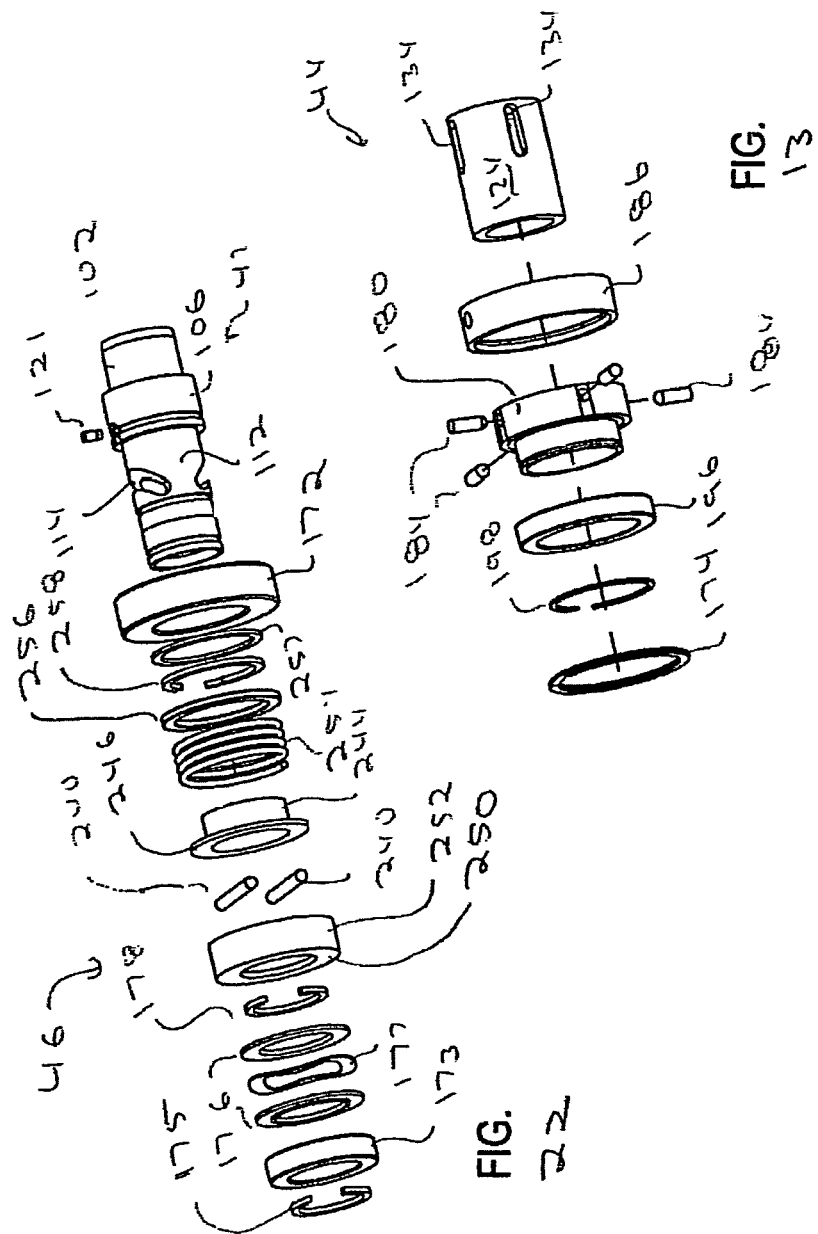

CUTTING ACCESSORY FOR A POWERED SURGICAL HANDPIECE, THE CUTTING ACCESSORY INCLUDING FEATURES TO FACILITATE THE ALIGNMENT OF THE ACCESSORY WITH THE HANDPIECE, HOLD THE ACCESSORY TO THE HANDPIECE, FACILITATE THE TRANSFER OF TORQUE TO THE ACCESSORY AND REDUCE THE WOBBLE OF THE ACCESSORY

RELATIONSHIP TO EARLIER FILED APPLICATION

This application claims priority under 35 U.S.C. Sec. 119 from U.S. Provisional Pat. App. No. 60/693,638 filed 25 Jun. 2005.

FIELD OF THE INVENTION

This invention relates to a surgical handpiece able to accept different rotating attachments and cutting accessories. More particularly, this invention is related to a surgical handpiece with a clutch for transferring rotational moment from a drive assembly that is compact in size. This invention is further related to a surgical handpiece with a coupling head for receiving different attachments or accessories that minimizes attachment/accessory rotational wobble.

BACKGROUND OF THE INVENTION

In modern surgery, an important instrument available to medical personnel is the powered surgical tool. Often, this tool is a handpiece in which a motor is housed. Secured to the handpiece is a cutting accessory designed for application to a surgical site on a patient in order to accomplish a specific medical task. Some powered surgical handpieces are provided with drills or reamers for cutting bores or other void spaces in tissue. The ability to use powered surgical tools on a patient lessens the physical strain of surgeons and other medical personnel when performing procedures on a patient. Moreover, most surgical procedures can be performed more quickly, and more accurately, with powered surgical tools than with the manual equivalents that preceded them.

One such type of tool is the surgical rotary handpiece. A rotary handpiece has spindle that rotates in response to actuation of the handpiece motor. Attached to the front end of the spindle is a coupling assembly. The coupling assembly releasably holds a device to the spindle so that the device rotates in unison with the spindle. Generally, two types of devices are releasably coupled to a handpiece spindle. One type of device is the actual cutting accessory, for example, the drill or the reamer. The cutting accessory has a shaft. The proximal end, the rear end, of the shaft is releasably held to the spindle by the coupling head.

The second type of device coupled to a rotary handpiece is a front end attachment. The attachment has a housing with opposed front and rear ends. An input shaft extends from the attachment rear end. The attachment front end has its own output spindle and complementary coupling assembly. Sometimes a gear assembly is located between the input shaft and the output spindle of an attachment. The gear assembly contains gears that typically increase the torque/decrease the speed of the rotational motion applied to the attached cutting accessory through the attachment output spindle. When the attachment is attached to the handpiece, the attachment housing is often statically coupled to the handpiece housing. The handpiece coupling assembly holds the attachment input shaft to the handpiece spindle. The actual cutting accessory is locked to the attachment spindle. The attachment speed reduces or speed increases the rotational moment output by the handpiece that is applied to the cutting accessory. Typically an attachment is used to speed reduce/torque increase the rotational moment of the attached cutting accessory.

Other attachments provide a means to attaching a cutting accessory to the handpiece spindle so the two components rotate at the same speed. An attachment of this variety typically does not have a gear assembly.

It is known to provide surgical handpieces with internal torque increasing/speed reducing gear assemblies. Some of these assemblies have plural output heads. This gear assembly receives the rotational moment from the motor output shaft and simultaneously rotates the plural output heads at different speeds. A clutch selectively connects the drill output spindle for rotation to one of the gear assembly output heads. The output speed/torque producing capability of the handpiece spindle is set by setting the clutch to selectively set the gear assembly-to-drill spindle connection. In some circumstances, these assemblies eliminate the need to employ a front head torque increasing/speed reducing attachment.

Known handpiece gear and clutch assemblies are relatively long in length. A disadvantage of this type of structure is that it increases the overall length of the handpiece. This runs contrary to a goal of efficient handpiece design, namely, the handpiece should be made as short as possible. This is because it easier for a surgeon to accurately position the working end of the cutting accessory that is relatively close to his/her hand than one further away. To provide this feature it is, therefore, desirable to construct a handpiece that has an overall length, especially from the motor forward, that is as compact as possible.

Moreover, a surgical handpiece is typically designed to be held at or near its center of gravity. This design reduces the physical stress to which the surgeon is exposed when he/she holds and needs to precisely position the tool in order to accomplish a given surgical procedure. The positioning of any mass away from a surgical handpiece's center of gravity/hand hold makes it more difficult for the surgeon to hold and precisely position the handpiece. Known gear and clutch assemblies, because of their lengths and masses, are typically off center from the center of gravity of the handpieces with which they are integral. During a surgical procedure, it may be necessary for the surgeon to precisely control a tool's position for an extended period. The off-center mass of a gear and clutch assembly can add to the physical stress to which the surgeon is exposed when so holding the tool.

Other disadvantages are associated with known coupling assemblies used to releasably hold cutting accessories and attachments to the handpiece spindles. Known coupling assemblies are effective for transmitting torque, rotational moment, from a handpiece spindle to the attached accessory/attachment and hold the accessory/attachment firmly to the spindle. Nevertheless, many coupling assemblies allow that shaft of the attached accessory/attachment to radially shift position, relative to the axis of the associated handpiece spindle.

The looseness of this fit allows the accessory/attachment to wobble when coupled to the handpiece. Wobble present in the shaft adjacent the surgical handpiece is amplified at the distal free end of the attachment, the end applied to the surgical site. Some attachments, for example reamers and drills used to perform certain procedures have lengths of 10 cm or more. The wobble, the radial shifting, at the distal end of these attachments can therefore be quite significant. The presence of this movement can appreciably add to the overall control the surgeon must exert in order to ensure that the working end of the attachment remains accurately position at the surgical site to which the attachment is applied.

SUMMARY OF THE INVENTION

This invention is related to a new and useful surgical rotary handpiece. The handpiece of this invention has both a clutch assembly that is compact in length and a coupling assembly that limits the wobble of the shaft of the complementary accessory/attachment fitted to the handpiece.

The clutch of the surgical rotary handpiece of this invention has moveable pins that selectively connect one of a plurality of the gear assembly drive heads to the handpiece output spindle for simultaneous rotation. A shifter positions the movable pins. A shift ring displaces the shifter. The moveable pins and members that transfer the motion from the shift ring to the shifter overlap. Collectively, these features combine to form a clutch of short axial length.

The coupling assembly of the handpiece of this invention is partially integral with the handpiece spindle. Internal to the spindle is a bore in which a coupling head of the attachment/accessory shaft is seated. The most proximal end of the surfaces of the spindle that define the bore and the most distal end of the coupling head are formed with complementary geometric features that force the transfer of torque, rotation movement, from the spindle to the shaft.

Extending forward, the coupling head is formed with a stabilizing body. This spindle bore is shaped so that the body is tightly fitted in the adjacent section of the bore. In some preferred versions of the invention, the stabilizing body and complementary bore-defining shaft inner wall have circular cross sectional profiles. Owing to the tight fit of the shaft in the bore, wobble of the shaft is minimized.

The accessory/attachment stabilizing body is formed with an indentation. In one version of the invention, this indentation is an annular groove that extends around the stabilizing body. The coupling assembly has retractable pins that extend into the spindle bore. The pins seat in the complementary stabilizing body indentation to releasably lock the accessory/attachment to the housing spindle.

BRIEF DESCRIPTION OF THE DRAWINGS

The invention is pointed out with particularity in the claims. The above and further features of this invention may be better understood by reference to the following detailed description taken in conjunction with the accompanying drawings in which:

FIG. 4 is an exploded view of the gear train of the surgical handpiece of this invention;

FIG. 5 is a cross sectional view of the gear train;

FIG. 10 is an end view of a rotary housing of the surgical handpiece of this invention;

FIG. 11 is a plan view of the rotary housing;

FIG. 12 is a cross section view of the rotary housing taken along line 12-12 of FIG. 11;

FIG. 13 is an exploded view of the components forming the clutch;

FIG. 22 is an exploded view of the coupling assembly;

DETAILED DESCRIPTION

Figure 1:
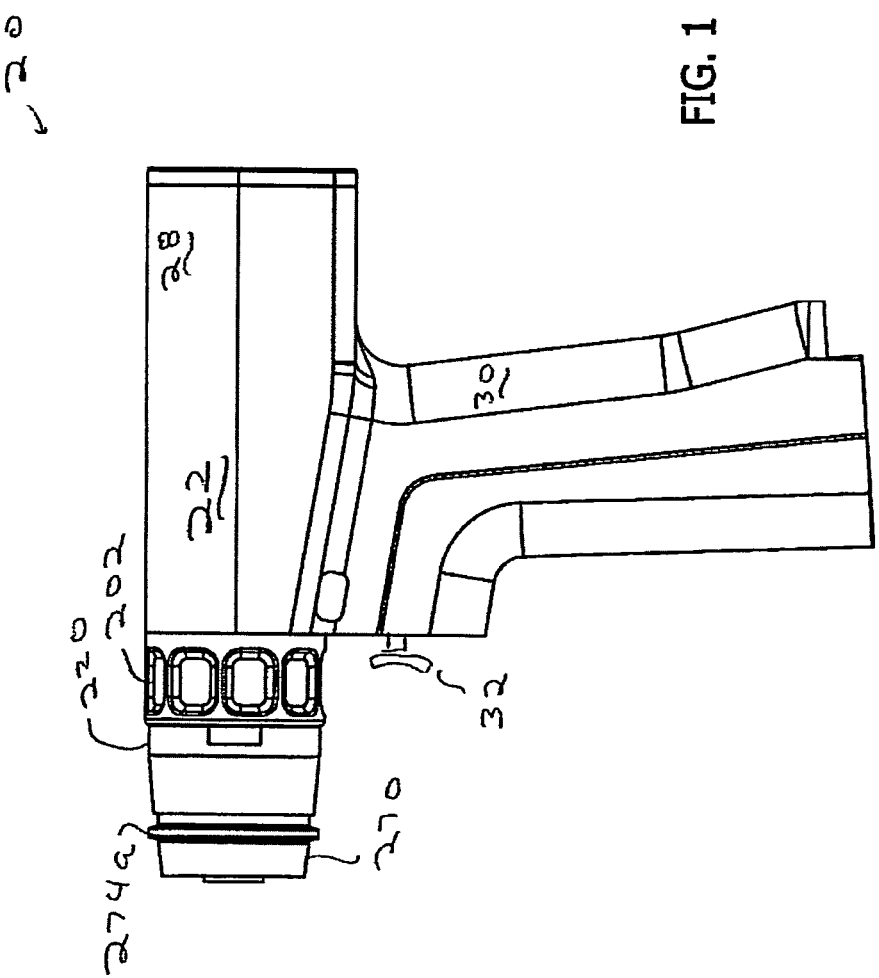
FIG. 1 is a side view of a surgical rotary handpiece of this invention to which a surgical accessory of this invention is attached.
Figure 2:
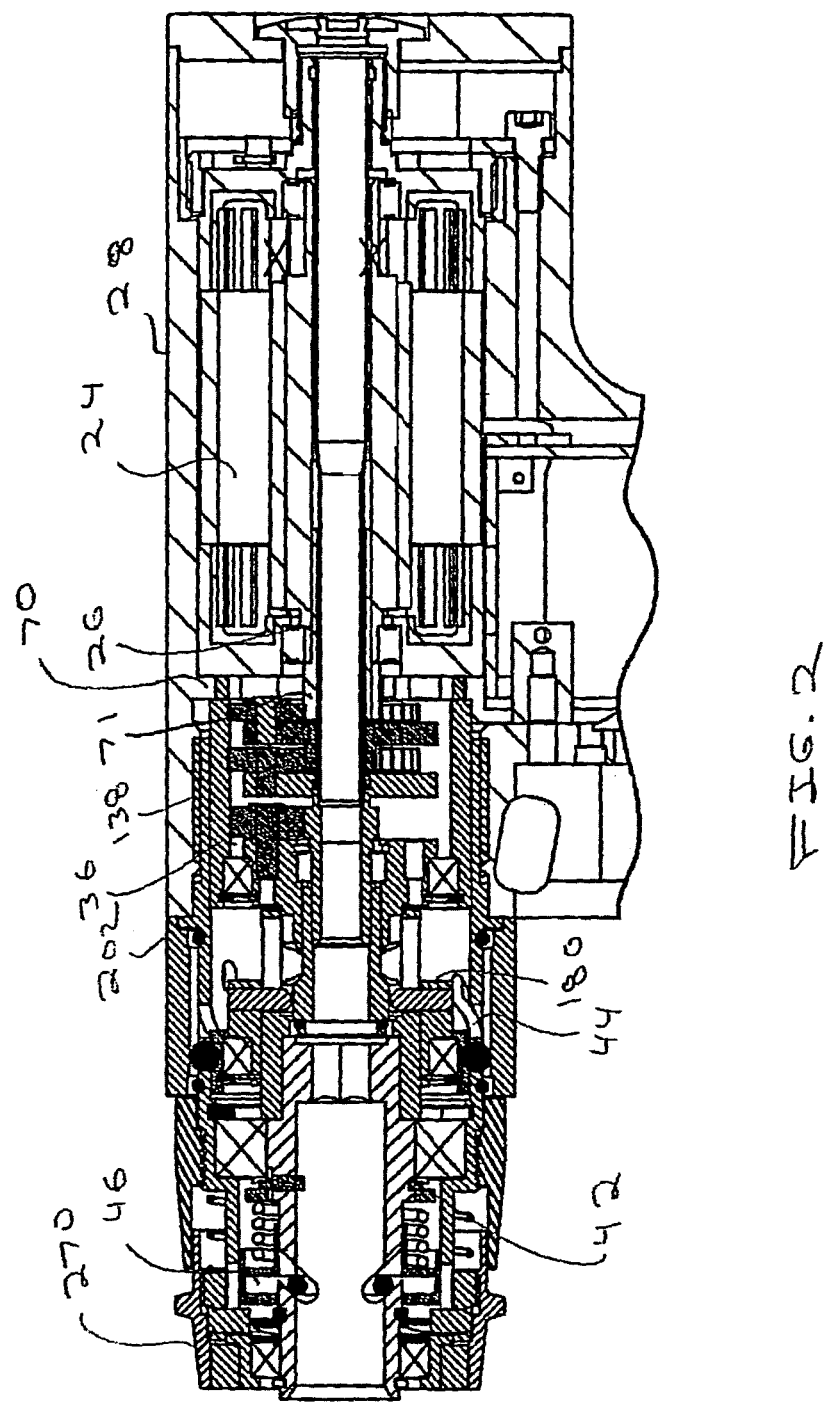
FIG. 2 is a cross sectional view of the front end of the handpiece along the longitudinal axis.

FIGS. 1 and 2 illustrate a rotary surgical handpiece 20 constructed in accordance with the invention. Handpiece 20 has a housing 22 in which in a motor 24 is seated. In one version of the handpiece 20, motor 24 is a DC motor. In other versions of the invention, motor 24 may be an AC motor, or a pneumatic or hydraulically driven motor. Integral with the motor 24 is rotating output shaft 26. Handpiece housing 22 is shaped to have a generally cylindrical head 28 in which motor 24 is fitted. Extending downwardly from head 28, handpiece housing 22 is shaped to have a handle 30 generally in the form of a pistol grip.

At least one trigger switch 32 extends distally forward from the front face of handle 30. ("Distal", it shall be understood means toward the surgical site to which the handpiece 20 is directed. "Proximal", means away from the surgical site.) A control circuit internal to the housing 22, (not illustrated and not part of this invention) monitors the actuation of the trigger switch 32. Based on the extent to which the trigger switch 32 is actuated, the control circuit selectively energizes the motor 24 to cause the output shaft to rotate at the desired speed.

A gear train 36 is connected to the exposed distally located front end of the motor shaft 26. Gear train 36 includes gears that reduce the speed and increase the torque of the rotational moment output by shaft 26. The gear train 36 has two rotating drive heads 86 and 92 (FIG. 4). Owing to the arrangement of the gears forming gear train 36, the rotation of motor shaft 26 causes drive heads 86 and 92 to simultaneously rotate at different speeds. Gear train 36 thus functions as a speed reduction assembly that outputs rotational force at two separate speeds.

Figure 2A:
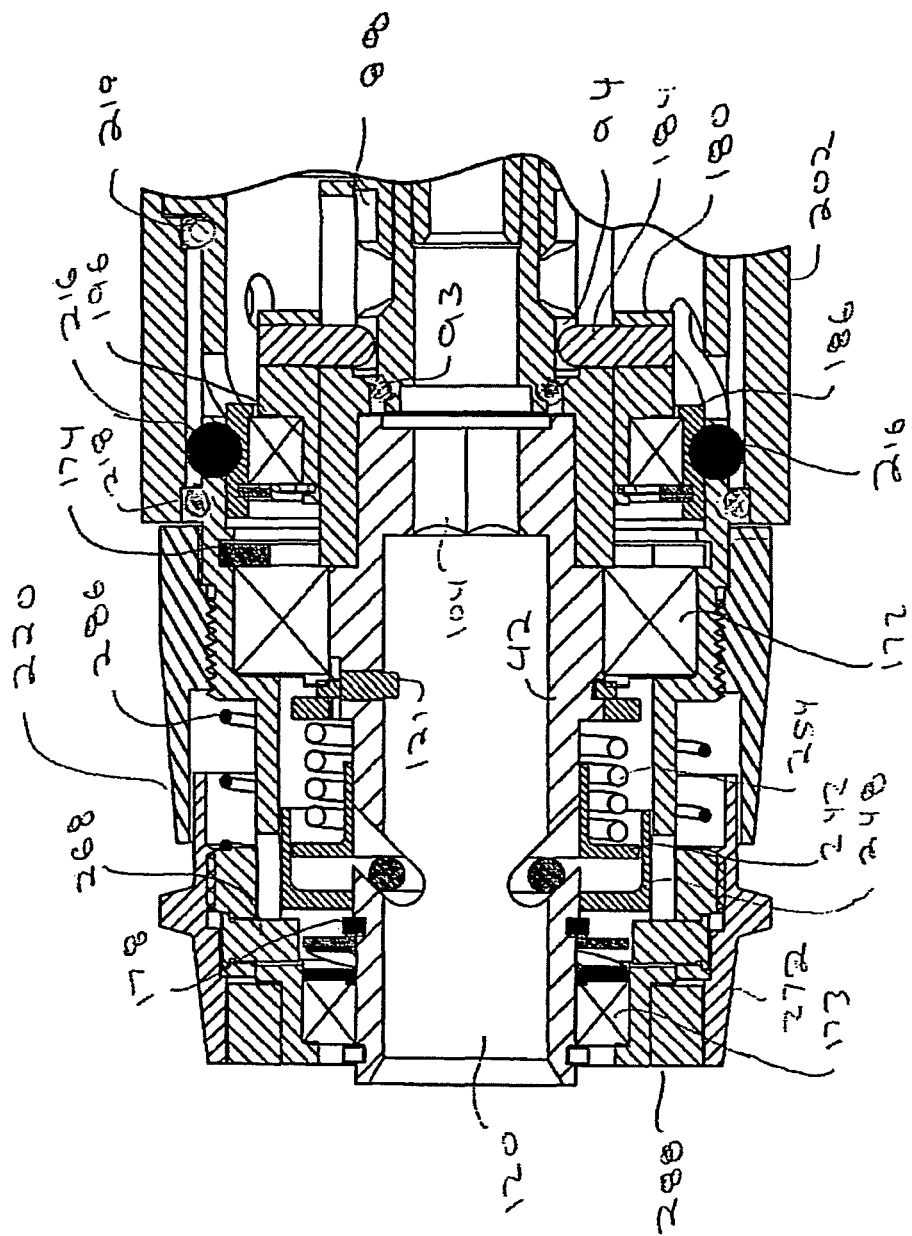
FIG. 2A is an enlarged cross sectional view of the distal end of the handpiece of FIG. 2.
Figure 3:
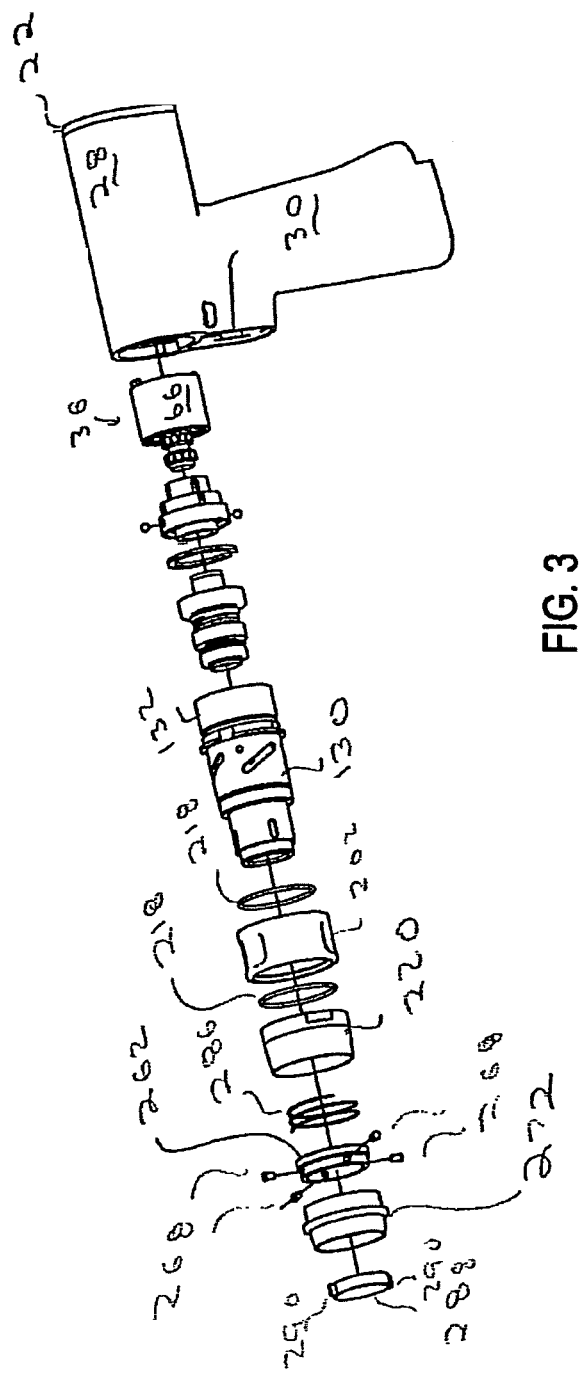
FIG. 3 is an exploded view of the distal front end of the handpiece.

With reference to FIGS. 2, 2A and 3 it can be seen that a spindle 42 is rotatably mounted to the housing head 28 forward of gear train 36. A clutch 44 selectively connects one of the two gear train drive heads 86 or 92 to spindle 42 so that the spindle and connected drive head rotate in unison.

Figure 27:
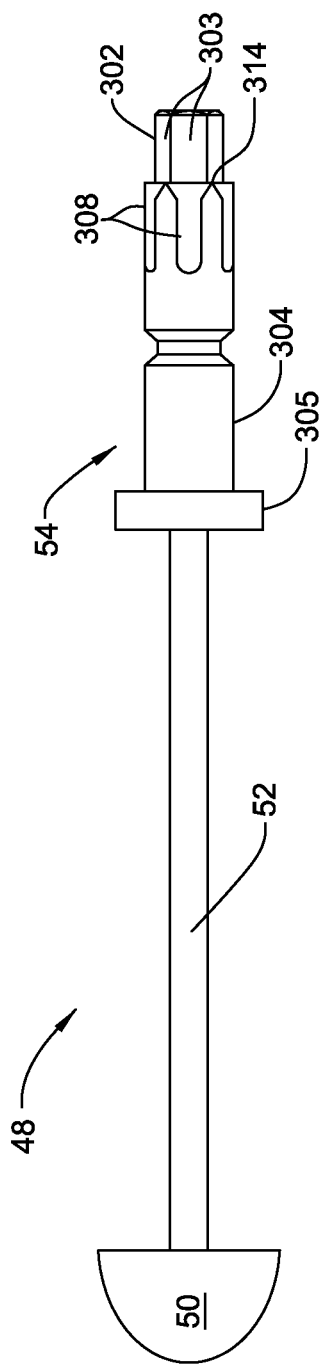
FIG. 27 is a plan view of a cutting accessory with the coupling head of this invention.

A coupling assembly 46 releasably holds a surgical attachment or a surgical cutting accessory 48, seen in FIG. 27 to the spindle 42. The particular cutting accessory 48 is an accetabular reamer. Again, it should be appreciated that this is exemplary, not limiting. Cutting accessory 48 has a distal end tissue working head 50, in the example, an accetabular reamer head. Extending proximally from tissue working head 50, cutting accessory 48 has an elongated shaft 52. A coupling head 54 is attached to the proximal end of shaft 52. Coupling head 54 is formed with geometric features that facilitate the rotational coupling of cutting accessory 48 to spindle 42 and minimize wobble of the accessory relative to the handpiece 30.

Surgical handpiece 20 of this invention is constructed so that the distal end of spindle 42 is formed with a bore 120 (FIG. 7) for receiving the attachment/accessory coupling head 54. Coupling assembly 46 locks the accessory coupling head 54 in spindle bore 120. As a consequence of this engagement, the coupling head 54, and therefore the whole of cutting accessory 48, rotates in unison with the spindle 42.

Gear train 36, now described by reference to FIGS. 3-5, includes a first set of three (3) planet gears 62 (two shown). Planet gears 62 are each rotatably mounted to a generally disc shaped planet carrier 64. Planet gears 62 and planet carrier 64, as with the remaining planet gears and planet carriers of gear train 36 are housed in a generally tubularly shaped ring gear 66. Ring gear 66 has a smoothed shaped outer wall and a toothed inner wall, (teeth not illustrated). The teeth of planet gears 62, as well as the teeth of the remaining planet gears 74 and 82, engage the teeth of ring gear 66.

Ring gear 66 is statically mounted in the handpiece housing head 28 forward of motor 24. To facilitate the static mounting of ring gear 66, the ring gear is formed with two proximally extending feet 68. The feet seat in openings formed in an internal structural web 70 of the housing to block rotation of the ring gear (openings not identified).

Planet gears 62 seat over and engage a gear pinion 71 disposed over motor shaft 26 (identified in FIG. 2). Thus, the rotation of motor shaft 26 results in the rotation of planet gears 62 and planet carrier 64.

A first sun gear 72 is integrally mounted to, concentric with and extends distally forward from planet carrier 64. Sun gear 72 engages a second set of three (3) planet gears 74 (two shown). Planet gears 74 are rotatably disposed around a second planet carrier 76. A tubular post 78 is integrally attached, concentric with and extends distally forward from second planet carrier 76. A set of teeth disposed around the proximal end base of post 78 form a second sun gear 80.

Second sun gear 80 engages a third set of planet gears, four (4) planet gears 82 (one shown). Planet gears 82 are rotatably attached to and disposed around a third planet carrier 84. A first drive head 86 is formed integrally with and extends axially forward from the third planet carrier. The first drive head 86 has a generally circular outer profile. The outer surface of drive head 86 is further shaped to have a plurality of longitudinally extending inwardly concaved, notches 88. The notches 88, which are circumferentially spaced apart, are located around the whole of the circumference of drive head 86. Planet carrier 84 is further formed to have an axially extending through bore 90. Bore 90 extends completely through both the planet carrier 84 and drive head 86.

A second drive head, drive head 92, is positioned distally forward of and is concentric with drive head 86. Drive head 92 has the same outer diameter as drive head 86. Drive head 92 is further shaped to notches 94 that have the same profile of notches 88 of the first drive head 86. A tubularly shaped stem 96 extends proximally rearward from drive head 92. In many versions of the invention, second drive head 92 and stem 96 are integrally formed. When gear train 36 is assembled, post 78 of the second planet carrier 76 is disposed in bore 90 of third planet carrier 84 and drive head 86. Stem 96 similarly is disposed in bore 90. More particularly, stem 96 is dimensioned to be tightly press fit over post 78. Thus, drive head 92 rotates in unison with the second planet carrier 76. Collectively, post 78 and stem 96 are shaped so that there is a longitudinal separation between drive heads 86 and 92.

Drive head 86 and stem 96 are further collectively shaped so that the outer surface of the stem is spaced inwardly of the adjacent bore 90 defining inner wall of the drive head. This arrangement allows stem 96 to rotate freely relative to the drive head 88. Adjacent the proximal end of stem 96, a bearing assembly 97 extends between post 78 and an adjacent inner circular wall internal to planet carrier 84. More particularly, the planet carrier internal wall against which the outer race of bearing assembly 97 seats defines an elongated groove 99 that is concentric with and has a large outer diameter than planet carrier bore 90. A retaining ring 100 disposed proximal to the bearing assembly 97 holds the bearing assembly in position. Retaining ring 100 is snap fitted in a groove 101 also formed in the interior of planet carrier 84. The planet carrier 84 is formed so that groove 101 is between the proximal end opening of bore 90 and groove 99 and is of greater diameter than groove 99.

Drive head 92 has a nose 91. Nose 91 extends forward of the portion of the drive head formed with notches 94. An O-ring 89 is disposed over nose 91. O-ring 89 is fitted over the drive head nose 91 portion immediately distal to the portion of the nose that defines notches 94.

A bearing assembly 95 rotatably holds planet carrier 84 to the static ring gear 66. Bearing assembly 95 has an outer race (not illustrated) seated in the perimeter of a counterbore 67 that forms the open end of ring gear 66. The inner race of bearing assembly 95 (not illustrated) seats against an annular step 98 formed in the outer perimeter of the third planet carrier 84. A retaining ring 87 holds bearing assembly 95 and, by extension, the moving components of gear train 36, in ring gear 66. Retaining ring 87 is snap fitted in a groove 93 formed in the inner wall of the ring gear 66 that defines counterbore 67.

Figure 6:
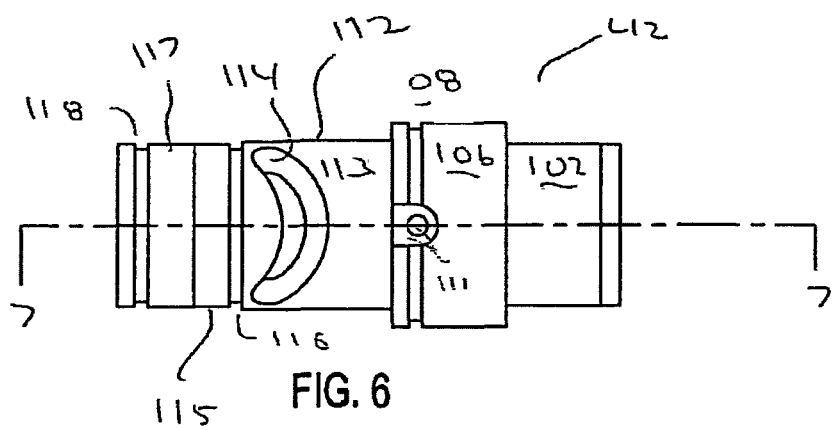
FIG. 6 is a plan view of the spindle of the surgical handpiece of this invention.
Figure 7:
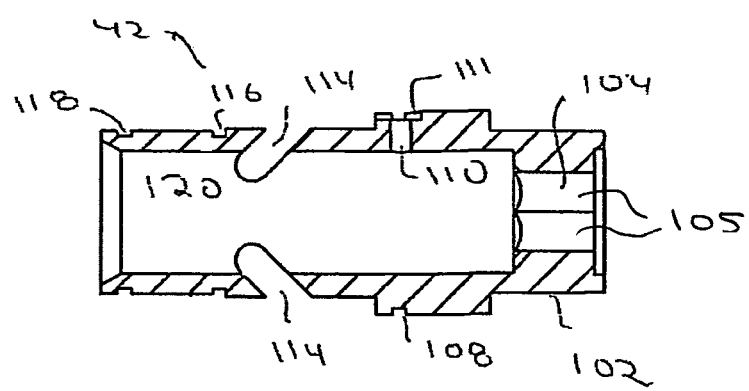
FIG. 7 is a cross sectional view of the spindle taken along line 7-7 of FIG. 6.

The structure of the spindle 42 is now described by reference to FIGS. 6 and 7. Generally, spindle 42 is formed from a single piece of metal that has circular sections of different diameters. At the most proximal end, spindle 42 has a head 102. Spindle 42 is further formed so that, internal to head 102 is a bore 104 with a hexagonal cross-sectional profile. The specific cross-section profile of bore 104 is not relevant to the basic structure of this invention. What is relevant is that bore 104 is shaped to closely slip fit receive the proximal end of the cutting accessory coupling head 54 fitted to the cutting accessory 48. The close fitting is required because the inner surfaces of the spindle 42, face surfaces 105, that define bore 104 are the surfaces that transmit the torque to the cutting accessory 48.

Extending distally from head 102, spindle 42 has a collar 106. Collar 106 is shaped to have an outer diameter greater than that of head 102. Immediately forward, proximal, of the distal end of the collar 106, the collar is shaped to have a groove 108 that extends circumferentially around the outer surface of the collar. Collar 106 is further formed to define an opening 110 that extends laterally through the collar. Opening 110 is located to extend through an arcuate section of the collar 106 that defines the base of groove 108. Opening 110 extends from a base of a recess 111 cut into the outer surface of collar 106.

Spindle 42 is further formed to have a stem 112 that projects distally forward from collar 106. Stem 112 has a number of sections with different outer diameters. A proximal section 113 adjacent collar 106 has a diameter approximately equal to that of sleeve head 102. Stem section 113 is formed to have two diametrically opposed receiving slots 114. Each receiving slot 114 is in a plane that, relative to the longitudinal axis of spindle 42, extends diagonally forward. In some versions of the invention, each slot 114 is in a plane that, relative to the longitudinal axis of the spindle 42, is at an angle of approximately 45°. Thus, as seen in FIG. 6, when viewing a slot 114 from the front, a slot 114 appears to have a curved profile.

Forward of section 113, the stem 112 is further formed to have a circumferential groove 116. Forward of groove 116 stem 112 has an intermediate section 115. Section 115 has a diameter slightly less than that of proximal section 113. The reduced diameter of stem section 115 allows below discussed wave spring 177 (FIG. 22) to freely flex.

Forward of section 115, spindle stem 112 is formed with a distal end section 117. Stem section 117 has an outer diameter between the diameters of sections 113 and 115. The inner race of a bearing assembly 173 (FIG. 2A) tightly fits over stem section 117. A groove 118 extends circumferentially around the outer surface of stem 112. Groove 118 is located immediately proximal to the distal end of stem section 117, which is also the distal end of spindle 42.

Spindle 42 is further formed to have a bore 120 that extends from the distal end, through stem 112 and collar 106 to bore 104. Bore 120 is concentric and contiguous with bore 104. In preferred versions of the invention, bore 120 has a circular cross sectional profile, though that need not always be the case. Bore 120 is dimensioned to facilitate the close slip fitting of a coupling head 54 of the cutting accessory 48 as discussed below.

A pin 121, seen in FIG. 13, is fitted in spindle opening 110 so as to be directed to the longitudinal center axis of the spindle 42. Pin 121 extends into bore 120

A generally tubular shaped outer coupler 124 is tightly fitted to the spindle 42, now described by reference to FIGS. 8 and 9. Outer coupler 124 has a constant outer diameter. The outer coupler 124 is further formed to have a proximal end bore 126 that extends distally forward from the proximal end of the coupler. In one version of the invention, proximal end bore 126 extends approximately half way through the length of the coupler. Output coupler 124 also has a distal end bore 128 that extends rearward from the distal end of the coupler. Distal end bore 128 has a diameter that facilitates the compression fitting of sleeve head 102 in the bore 128.

Between the proximal end and distal end bores 126 and 128, respectively, output coupler 124 is formed to have a circular void space 127. The outer perimeter of void space 127 is defined by a circular flange 129 that extends inwardly from the inner walls of coupler 124 that define bores 126 and 128 and space 127. The distally-directed laterally extend annular face of flange 129 is the surface against which the proximally directed face of sleeve head 102 abuts. Outer coupler 124 is further formed to have four longitudinally extending slots 134. Each slot 134 extends from the outer surface of the coupler 124 into the proximal end bore 126. Slots 134 are equangularly spaced apart from each other around the perimeter of the outer coupler 124.

Outer coupler 124 itself is shaped to have an outer diameter that is slightly greater than the outer diameter of spindle collar 106. When the spindle head 102 is fit in the outer coupler 124, the distal end face of the outer coupler forms an annular step around the proximal end of the spindle collar 106.

Returning to FIG. 2, it can be seen that, when surgical handpiece 20 of this invention is assembled, the spindle 42 and outer coupler 124 sub-assembly are fitted in the housing 32 so that gear train drive heads 86 and 92 are disposed in the proximal end bore 126 of the outer coupler. Outer coupler 124 is shaped so that the inner wall that defines the proximal end bore 126 is spaced away from the drive heads 86 and 92. Drive head nose 91 seats in outer coupler void space 127. O-ring 93 abuts the adjacent inner face of coupler flange 129.

Gear train 36, outer coupler 124 and spindle 42 are substantially disposed in a rotary housing 130 that extends distally forward from the front of handpiece housing 22. The rotary housing 130, now described by reference to FIGS. 10-12, is formed from a single piece of metal that has a number of circular cross-sectional sections. The most proximal section of the rotary housing 130 is a base 132. The outer surface of rotary section base 132 adjacent the proximal end of the rotary section is formed with threading 137 (seen in FIG. 11 only). Base 132 is formed with an open ended bore 136. Bore 136 is dimensioned to facilitate the loose slip fitting of the base over gear train ring gear 66. When handpiece 20 is assembled, base threading 137 engages complementary threading 138 formed around an inner wall of housing 28 (FIG. 2). This threaded engagement holds rotary housing 130 to the handpiece housing 22.

Extending distally of the threaded section, rotary housing base 132 is formed with a section 140 with a smooth outer wall. Forward of base section 140, the rotary housing 130 has a flange 142 that extends radially outward of base 132. Flange 142 is the structural component of the rotary housing 130 that stops proximal movement of the rotary housing when the housing is screw fitted to the handpiece housing 22. Rotary housing 130 is further formed to define four slots 144 that extend through base section 140 and flange 142. Slots 144 are equangularly spaced apart. The slots 144 function as spaces for receiving a fastening tool (not illustrated) used to screw secure the rotary housing 130 to the handpiece housing 22 during manufacture.

Forward of flange 142, rotary housing 130 forms a clutch sleeve 146. Clutch sleeve 146 has a diameter slightly less than that of base 132. The clutch sleeve 146 is formed to have four equangularly spaced apart slots 148. Slots 148 extend diagonally downwardly around the outer circumference of the clutch sleeve 146. Four equangularly spaced apart holes 150 are also formed in the clutch sleeve 146. Holes 150 are in a common circumferential section of the clutch sleeve located proximal to the proximal ends of slots 148. Holes 150 are provided to facilitate manufacture and disassembly of the handpiece 20.

A groove 152 is formed in the clutch sleeve 146 to extend circumferentially around the outer surface of the sleeve. Groove 152 is located proximally rearward of the forward distal end of the clutch sleeve 146. The outer surface of the clutch sleeve 146 located distal to groove 152 and extending to the distal end of the clutch sleeve is provided with threading 154 (seen in FIG. 11 only).

Projecting distally forward of clutch sleeve 146, rotary housing 130 has a coupling neck 156. Coupling neck 156 has a diameter less than that of clutch sleeve 146. The coupling neck 156 is formed to define four equangularly spaced apart slots 158. Slots 158 extend longitudinally along the coupling neck 156 and are generally located in the most distal portion of the coupling neck 158.

A head 160 forms the most distal section of rotary housing 130. Head 160 extends forward from and has a diameter less than that of coupling neck 156. Head 160 is formed with an inwardly directed circumferential lip 162. Lip 162 defines the open distal end of the rotary housing, (distal end opening not identified).

Rotary housing 130 is further formed so that extending axially, distally forward from bore 136 there is a bore 166 that extends to the distal end of the housing. Bore 166 has sections of different diameters. The diameters of the different bore sections (not identified) are generally sized relative to each other in the same manner the outer diameters of the clutch sleeve 146 and coupling neck 156, and head 160 correspond to each other. The rotary housing 130 is further formed to have a groove 168 that extends inwardly from a housing inner wall that defines one of the sections of bore 166. Specifically, groove 168 is formed in the housing clutch sleeve 146 so as to be immediately distal to the circular slice of the sleeve 146 in which outer circumference groove 152 is formed.

Bearing assemblies 172 and 173, seen best in FIGS. 2A and 13, rotatably hold the spindle and outer coupler sub-assembly to the rotary housing 130. The outer race of bearing assembly 172 (outer race not illustrated) seats against the bore 166— defining inner wall of the housing clutch sleeve 146. The proximal end of the bearing race seats against the stepped inner annular surface of the rotary housing between the clutch sleeve 146 and the coupling neck 156. The proximally-directed face of the outer race of bearing assembly 172 abuts a retaining ring 174 disposed in bore 166. Retaining ring 174 is snap fitted in rotary housing groove 168.

The inner race of bearing assembly 172 (not illustrated) is press fit over spindle collar 106. When the handpiece 20 of this invention is assembled, the proximal end of the inner race of bearing assembly is disposed against the annular portion of the distally directed face of the adjacent outer coupler 124. As discussed above, the outer race of bearing assembly 172 is blocked from distal movement by the adjacent inner walls of the rotary housing 130. Thus, the abutment of the outer coupler 124 against the inner race of bearing assembly 172 by extension blocks distal movement of the spindle and outer coupler sub-assembly.

Bearing assembly 173 extends between the distal front end of spindle stem 112 and the adjacent inner wall of the rotary housing head 160. The outer race of bearing assembly 173 (race not illustrated) seats against the inner wall of the rotary housing 130 within the housing head 160. The bearing assembly outer race also abuts the proximally directed surface of rotary housing lip 162. The distally directed face of the inner race of bearing assembly 173 seats against a retaining ring 175. Retaining ring 175 is snap fitted into groove 118 of spindle stem 112. Thus, collectively, rotary housing lip 162 and retaining ring 175 block forward movement of bearing assembly 173.

Washers 176 and 177 and retaining ring 178 cooperate to prevent proximal movement of bearing assembly 173. Two washers 176 are provided. The more distal of the two washers 176 is disposed against the proximally-directed face of the bearing assembly 173. Washer 177, which is flexible wave washer, is sandwiched between the distal and proximal washers 176. The retaining ring 178 seats in spindle groove 116.

The retaining ring 178 extends above the outer surface of the surrounding spindle sleeve 112. When handpiece 20 is assembled, the exposed portion of the retaining ring 178 blocks proximal movement of washers 176 and 177 and, therefore, similar movement of bearing assembly 173. Wave washer 177 is provided to ensure that, in the event of manufacturing variations, the distal washer 176 is disposed against the bearing assembly 173.

Washers 176 are L-shaped. The short vertical sections of the washers 176, (not identified) are disposed around the outer surface of the spindle stem 112. The washer 176 closest to bearing assembly 173 is positioned so its vertical section is against the inner race of the bearing assembly. This arrangement holds the washer 176 off the inner race of the bearing assembly 173. The washer 176 adjacent retaining ring 178 is positioned so that its vertical section abuts the retaining ring.

When the spindle and outer coupler sub-assembly is so positioned, gear train drive heads 86 and 92 are both seated in the outer coupler proximal end bore 126. Slots 134 are formed in the outer coupler 124 so as to extend over the drive heads 86 and 92. Also, the components of this invention are dimensioned so that when the spindle 42 is seated in the rotary housing 130, the most distal end of the spindle projects a slight distance forward of the surrounding distal end of the rotary housing.

Figure 14:
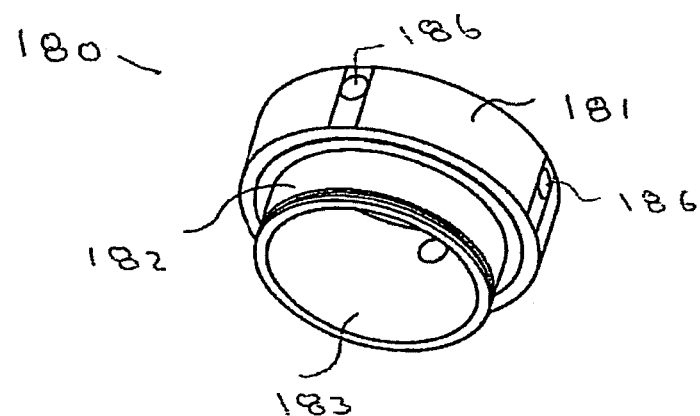
FIG. 14 is a perspective view of the inner shifter of the clutch of this invention.
Figure 15:
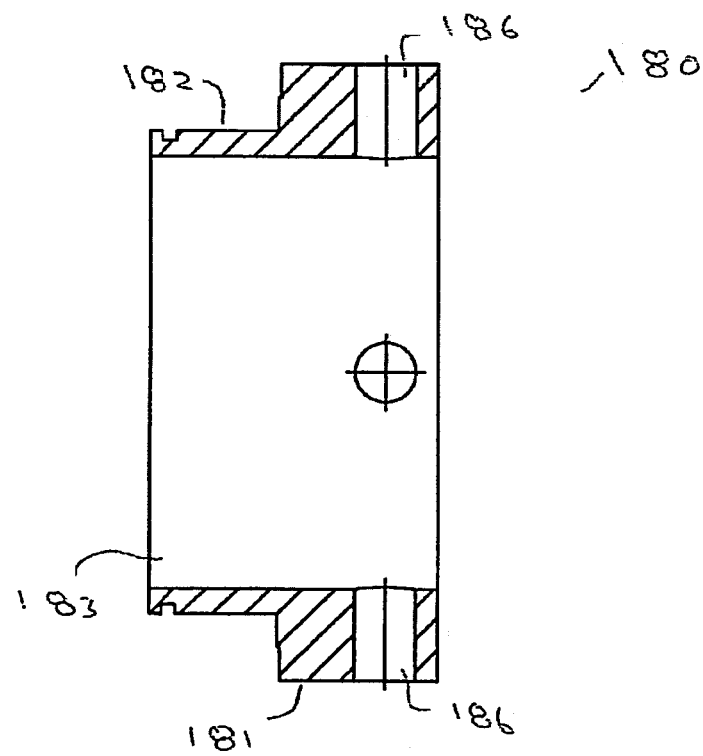
FIG. 15 is a cross sectional view of the inner shifter.

The construction of the clutch 44 is now described by reference to FIGS. 2A and 13. The clutch includes a circular inner shifter 180 disposed inside the rotary housing clutch sleeve 146 over the outer coupler 124. As best seen in FIGS. 14 and 15, inner shifter has a proximal end base 181. Extending distally forward from base 181, the inner shifter 180 is shaped to have a head 182. Head 182 has an outer diameter less than that of base 181. A constant diameter bore 183 extends axially through the inner shifter 180 from the proximal end of base 181 to the distal end of head 182.

Inner shifter 180 is shaped so that when the outer coupler 124 is seated in bore 183, the shifter is able to move longitudinally along the length of the outer coupler. Clutch 44 includes four equangularly spaced apart torque pins 184 that extend radially inwardly from the inner shifter base 181. Each torque pin 184 is seated in a laterally extending opening 185 formed in the inner shifter base 181. Each torque pin 184 extends through an associated one of the outer coupler slots 134. Torque pins 184 are of sufficient length so end tips of the pins can seat in notches 88 and 94 of, gear train drive heads 86 and 92, respectively.

Figure 16:
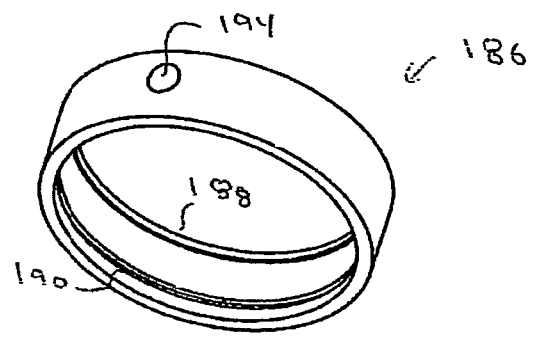
FIG. 16 is a perspective view of the shifter housing.
Figure 17:
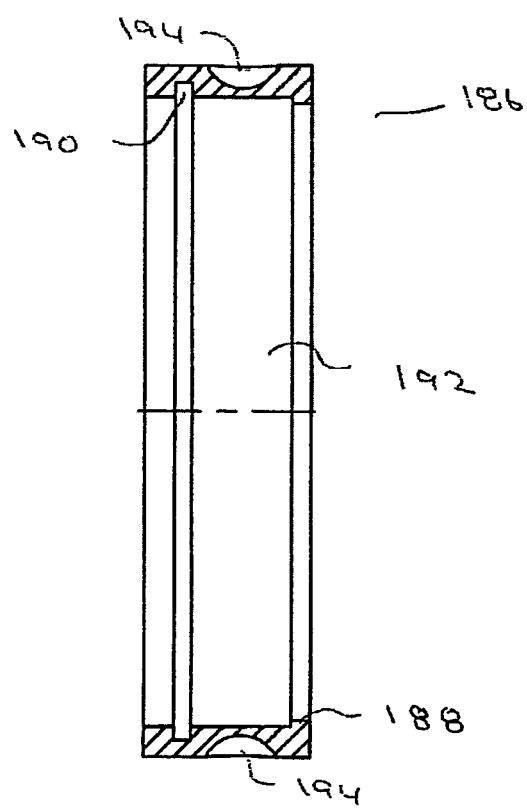
FIG. 17 is a cross sectional view of the shifter housing.

A shifter housing 186 disposed over the inner shifter 180 longitudinally moves the inner shifter 180 over the outer coupler 124. The shifter housing 186, now described by reference to FIGS. 16 and 17, is generally in the form of a constant outer diameter, ring shaped structure. Shifter housing 186 is further formed to, at the proximal end, have an inwardly extending lip 188. A groove 190 extends inwardly from the annular inner wall of the shifter housing 186 that defines the center opening 192 through the housing. Groove 190 is located proximal to the distal end face of the shifter housing 186. The shifter housing 186 is further formed to define, on the outer surface, two diametrically opposed spherical indentations 194.

Shifter housing 186 is disposed in the rotary housing clutch sleeve 146. Inner shifter head 182 is positioned inside the shifter housing 186. A bearing assembly 196 is disposed between the outer circumferential wall of the inner shifter head 182 and the adjacent inner wall of the shifter housing 186. The proximal end of bearing assembly 196 abuts the adjacent distally-directed annular surface of the inner shifter base 181 that projects radially beyond head 182. The outer perimeter of the distally directed face of bearing assembly 196 abuts a retaining ring 198 fitted to the shifter housing 186. Specifically, retaining ring 198 is snap fitted in shifter housing groove 190. Thus, the capture of the opposed ends of bearing assembly 196 by the inner shifter base 181 and retaining ring 198 lock the inner shifter 180 and shifter housing 186 together for longitudinal movement. Bearing assembly 196 allows the inner shifter 180 and shifter housing 186 to axially rotate relative to each other.

Figure 18:
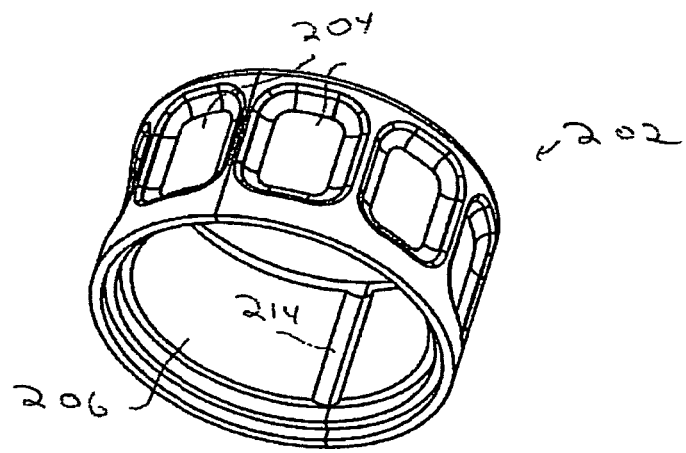
FIG. 18 is a perspective view of the shift ring.
Figure 19:
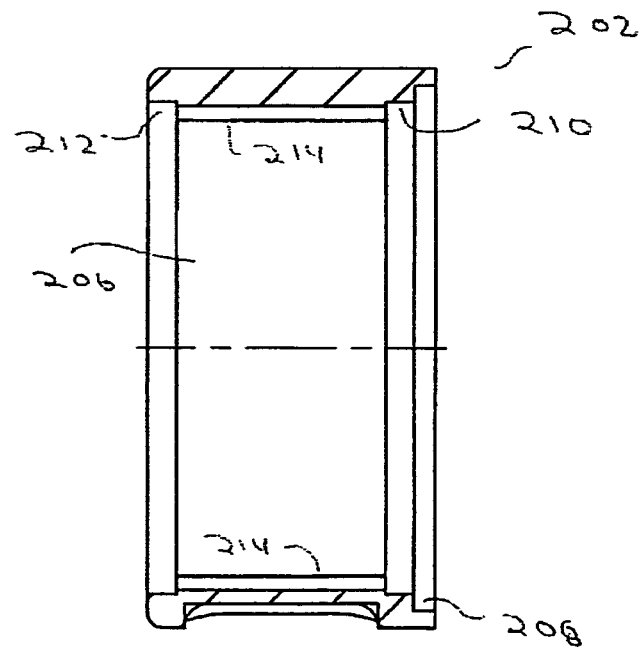
FIG. 19 is a cross sectional view of the shift ring.

A shift ring 202 rotatably mounted over the rotary housing clutch sleeve 146 is manually actuated to set the longitudinal position of the shifter housing 186 and, by extension, the inner shifter 180. Seen best in FIGS. 18 and 19, the shifter ring 202 is generally in the form of a tubular member. Indentations 204 formed in the outer surface of the shifter ring 202 facilitate the finger grasping of the ring. The shifter ring 202 is further shaped to define an axially extending through bore 206. Bore 206 is dimensioned to allow the shift ring 202 to rotate over the underlying rotary housing clutch sleeve 146. At the proximal end, shifter ring defines a first counterbore 208 that defines the proximal end opening into bore 206. A second counterbore 210 is located between the first counter bore 208 and bore 206. The second counterbore 210 has a diameter between that of bore 206 and counterbore 208.

At the distal end, shift ring 202 is formed to have a third counterbore 212. The third counterbore 212 forms the distal end opening into bore 206. The second and third counterbores 210 and 212, respectively, are of identical diameter. The inner wall of shift ring 202 that defines bore 206 is further formed to define two longitudinally extending, diametrically opposed concave grooves 214. Each groove 214 extends from the second counterbore 210 to the third counterbore 212.

When handpiece 20 of this invention is assembled, ball bearings 216 transfer the rotational motion of shift ring 202 into axial motion that displaces the shifter housing 186. Each ball bearing 216 is seated in opposed ones of the rotary housing clutch sleeve slots 148. Two ball bearings 216 are provided; there are four slots 148. The additional slots 148 aid component orientation during assembly of the handpiece 20. Inside the rotary sleeve 130, each ball bearing 216 seats in a separate one of the indentations 194 formed in the shifter housing 186. Outside of rotary housing 130, each ball bearing 216 seats in a separate one of the grooves 214 formed in shift ring 202.

When handpiece 20 of this invention is assembled, rotary housing flange 142 seats in the shift ring first counterbore 208. O-rings 218 extend between the outer circumferential face of rotary housing 130 and the inner walls of shift ring 202. A first O-ring 218 is seated in the annular space of shift ring second counterbore 210. The second O-ring 218 is seated is seated in the shift ring third counterbore 212. Both O-rings 218 extend over the smooth outer surface of the rotary housing clutch sleeve 146.

Figure 20:
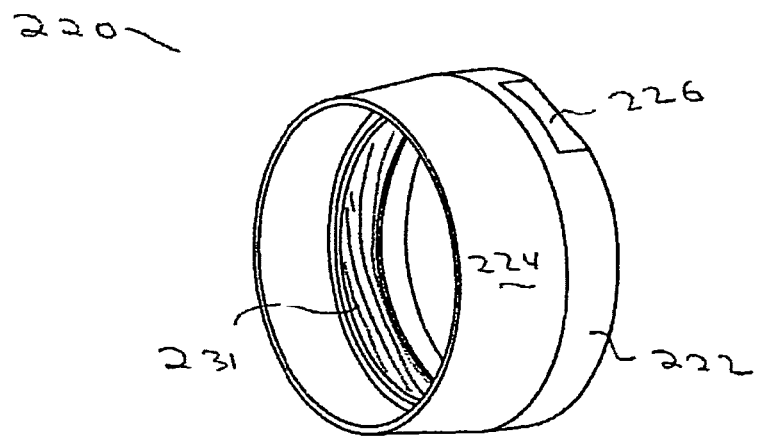
FIG. 20 is a perspective view of the shift ring nut.
Figure 21:
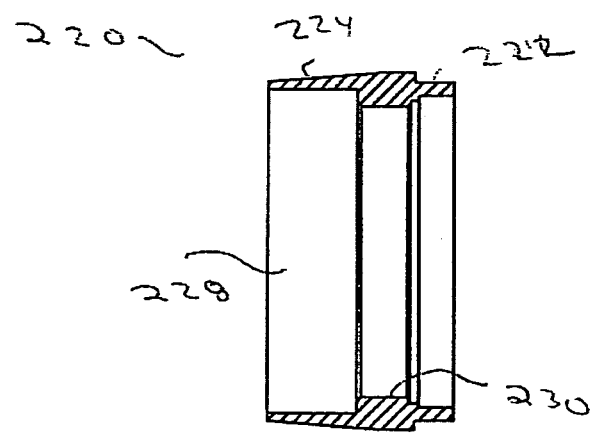
FIG. 21 is a cross sectional view of the shift ring nut.

A shift ring nut 220 holds the shift ring 202 to the rest of the handpiece 20. Shift ring nut 220, best seen in FIGS. 20 and 21, is generally tubularly shaped. The shift ring 220 is formed to have a base 222 with a generally constant outer diameter. Forward of base 222 shift ring nut 220 has a head 224. Extending distally forward, the outer diameter of the shift ring head 224 tapers inwardly. The shift ring 220 is further formed to define two opposed flats 226 in the proximal end of the outer surface of base 222. Flats 226 receive a fastening tool used to screw secure the shift nut 220 to the rotary housing 130 during assembly.

Bore 228 extends axially through the shift ring nut 220 from the proximal end to the distal end. The shift ring is further formed to have an inwardly stepped annular lip 230 that extends inwardly from the inner circular wall that defines bore 228. The inner round face of lip 230 is formed with threading 231 (seen in FIG. 20). The shift ring nut 220 is screw secured to the rotary housing by engaging shift ring nut threading 231 with threading 154 on the rotary housing clutch sleeve 146.

An understanding of the coupling assembly 46 of the surgical handpiece of this invention is now obtained by initial reference to FIGS. 2A, 3 and 22. Specifically, coupling assembly 46 includes two cylindrical retaining pins 240 each of which is seated in one of the spindle slots 114. When pins 240 are in the most forward position in slots 114, the pins seat in a groove (indentation) 306 formed in the coupling head 54 of the attachment/accessory attached to the handpiece 20. Pins 240 thus hold the attachment/accessory to the tool spindle 42.

An inner washer 242 and outer washer 248 are the components of coupling assembly 46 that releasably hold retaining pins in slots 114 and attachment/accessory indentation 306. Inner washer 242 is shaped to have along any one slice thereof an L-shaped cross sectional profile. More specifically, the inner washer has cylindrical base 244 that extends over the spindle stem 112. The spindle 42 and inner washer 242 are dimensioned relative to each other such that the inner washer can freely move longitudinally over the spindle. Inner washer 242 is further shaped to have a lip 246 that extends perpendicularly outwardly from the distal front end of base 244.

Inner washer 242 nests in the outer washer 248, also disposed over the spindle stem 112. The outer washer is shaped to have flat, circularly shaped head 250. Extending proximally rearwardly from the outer perimeter of the head 250 and formed integrally with the head is a cylindrically shaped skirt 252. The outer washer 248 is positioned over the spindle stem 112 so that the washer head 250 is generally aligned with the distal ends of the spindle slots 114. The distal end of the inner washer 242 is disposed in the annular space defined by the outer wall of the spindle stem 112 and the inner wall of skirt 252 of the outer washer 248.

A coil spring 254 disposed around the spindle stem 112 normally urges the inner washer 242 towards the outer washer 248. The proximal end of spring 254 seats against a washer 256 seated over the most distal portion of the spindle collar 106. The proximally-directed face of washer 256 abuts a retaining ring 258. Retaining ring 258 is snap fitted in spindle groove 108 and projects beyond the outer surface of the spindle collar 106. The retaining ring 259 thus stops proximal movement of washer 256 and, by extension, spring 254. A washer 257 is disposed between the proximally directed face of retaining ring 258 and the adjacent distally directed face of the inner race of bearing assembly 172.

Spring 254 thus urges the inner washer 254 forward. This movement of the inner washer 254 first compression traps the retaining pins 240 trapped between the inner and outer washers 242 and 248, respectively. The continued force imposed by the spring 254 continues to urge washers 242 and 248 and pins 240 forward. As a result of this forward movement of this sub assembly, pins 240 are held in a forward distal section of spindle slots 114. The distal forward movement of this sub-assembly is stopped by the abutment of retaining pins 240 against the inner surfaces of the stem sleeve 112 that define the distal perimeters of slots 114. When pins 240 are so positioned, each pin extends into spindle bore 120.

Figure 23:
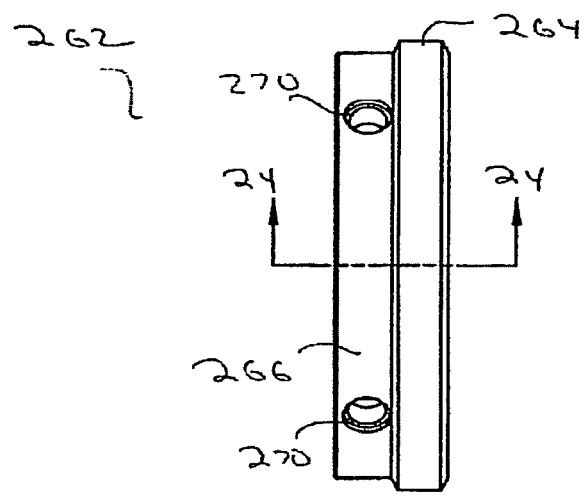
FIG. 23 is a side view of the coupling assembly actuating ring.
Figure 24:
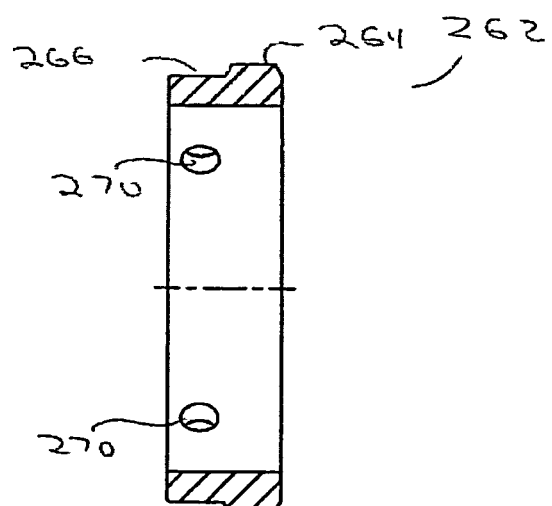
FIG. 24 is a cross sectional view of the actuating ring.

An actuating ring 262 selectively moves washers 242 and 248 and, by extension, pins 240 away from the attachment/accessory indentation 306 in which they are seated. The actuating ring 262 extends circumferentially around the outer perimeter of the distal end of the rotary housing coupling neck 156. Now described in detail by reference to FIGS. 23 and 24, the actuating ring 262, which is generally ring shaped, is formed to have a proximal end base 264. The outer circumferential surface of the actuating ring base 264 is provided with threading, (not illustrated). Actuating ring 262 is further formed so that extending distally forward of base 264 there is a neck 266. Neck 266 has an outer diameter less than that of the base 264. The inner wall that defines the through bore through the actuating ring 262 (bore and inner wall not identified) is of a constant diameter along the length of the sleeve.

Four equangularly spaced apart pins 268 are mounted in radial openings 270 formed in the actuating ring neck 266. Pins 268 are directed inwardly towards the axial center of the actuating ring 262. When handpiece 20 of this invention is assembled, pins 268 extend through slots 158 formed in the rotary housing coupling neck 156. The seating of pins 268 in the rotary housing slots 158 limits the range of proximal and distal movement of the actuating ring 262. Pins 268 are of sufficient length that, when the actuating ring 262 is moved proximally rearward, the free ends of the pins press against the distally directed face of head 250 of the outer washer 248.

Figure 25:
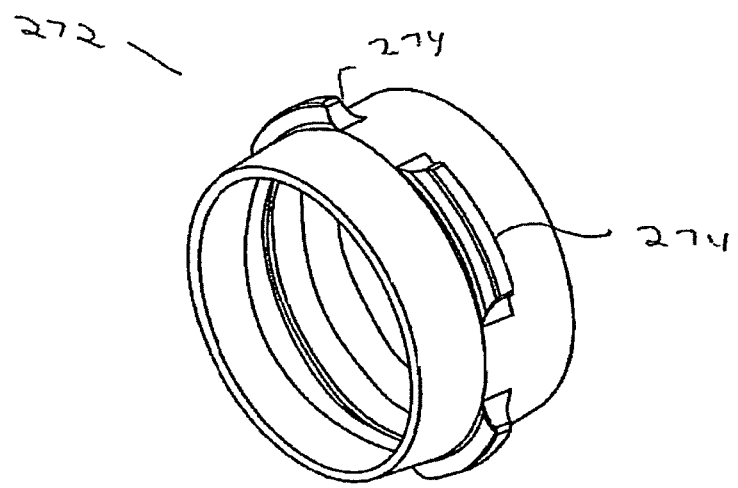
FIG. 25 is a perspective view of the actuating sleeve.
Figure 26:
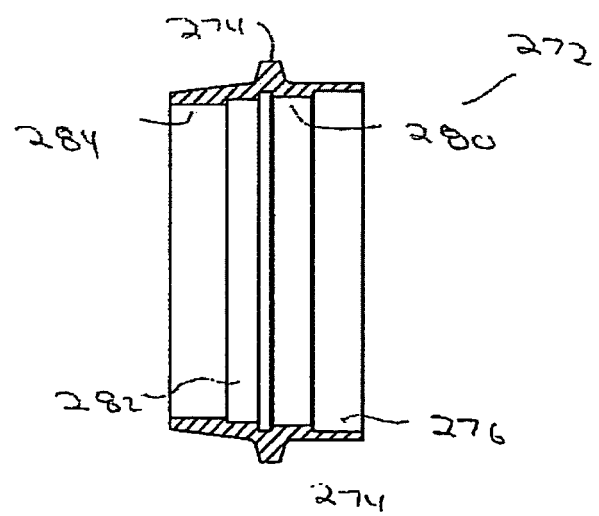
FIG. 26 is a cross sectional view of the actuating sleeve.

An actuator sleeve 272 functions as a handhold that allows the surgical personnel to move the actuating ring 262. As seen in FIGS. 25 and 26, the actuator sleeve 272 is formed so as to have along the outer surface thereof four spaced apart tabs 274. Tabs 274 function as finger holds that allow personnel to hold and rearwardly depress the actuator sleeve 272. In the sleeve of FIG. 1, a single circumferential lip 274a performs the same function as tabs 274.

The actuator sleeve 272 has an axially extending bore that extends completely through the sleeve. The bore has a first proximal end section 276. Forward of section 278 the bore has a second section 280. Section 280 has a diameter less than that of bore section 278. The inner wall of the actuator sleeve 272 that defines bore section 280 has threading, (not illustrated). Forward of bore section 280, actuating sleeve 272 is formed to have a bore section 282. (Between bore sections 280 and 282 there is a groove, not identified, present for manufacturing reasons.) Bore section 282 has an outer diameter less than that of bore section 280. Bore section 284, is the most distal section of the actuating sleeve through bore. Bore section 284 has a diameter less than that of bore section 282.

When the handpiece 20 is assembled, the actuator sleeve 272 is secured to and over the actuating ring 262. Specifically, the threaded surface that defines bore section 280 of the actuator sleeve 272 is screw secured to the threading on outer surface of the actuating ring base or ring base 264.

A coil spring 286 normally holds the actuating ring 262 distally forward, away from the outer washer 248. Spring 286 is disposed between the rotary housing coupling neck 156 and the shift ring nut 220. The proximal end of coil spring 282 seats against the outer annular step surface between the rotary housing coupling clutch sleeve 146 and the coupling neck 156. The distal end of spring 286 seats against the proximally directed face of the actuating ring base 264. Spring 286 urges actuating ring forward so as that pins 268 are normally spaced away from outer washer 248.

A torque ring 288 is press fit over the rotary housing head 160. Torque ring 288 is formed with two opposed laterally extending tabs 290. When the handpiece 20 is assembled the whole of the torque ring 290 is normally disposed in bore section 284 of the actuating sleeve 272. Torque ring 288 is shaped so that tabs 290 do not abut, and therefore do not restrict the movement of the actuating sleeve 272. When an attachment is fitted to handpiece 20, at least one torque ring tab may seat in a complementary notch formed in an exposed static component of the attachment. This engagement prevents the static elements of the attachment from rotating relative to the handpiece 20. In alternative versions of the invention, torque ring 288 has a single tab 290 or three or more tabs 290.

Figure 27A:
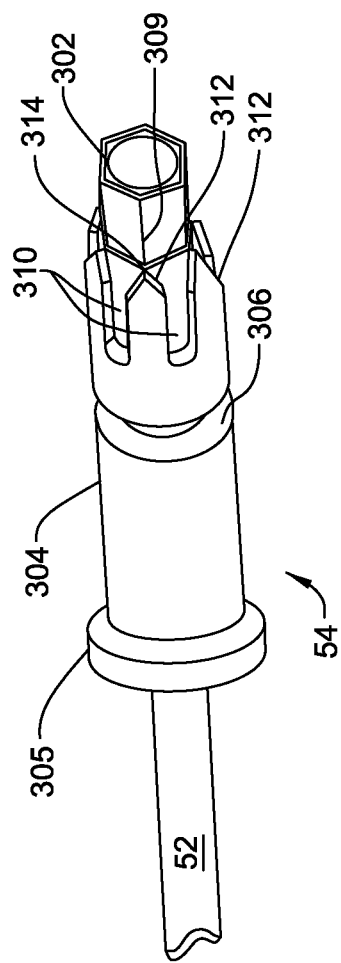
FIG. 27A is a perspective view of the coupling head of the cutting accessory.

The cutting accessory 48 constructed in accordance with this invention is now described by reference to FIGS. 27 and 27A. The cutting accessory 48 has an elongated shaft 52. The coupling head 54 is integrally attached to the proximal end of the shaft 52. Coupling head 54 has the features that both receive the torque generated by the handpiece 20, facilitate the locking of the cutting accessory 48 to the handpiece and inhibit the generation of accessory wobble.

The tissue working head 50 is attached to the distal end of the shaft 52. In the illustrated version of the invention, the tissue working head 50 is an accetabular reamer. It is understood that this is exemplary not limiting. In other versions of the invention, the tissue working head may be other members such as a drill head or a bur. Also, it should be understood that in some versions of the invention, the tissue working head may be releasably attached to the shaft 52. For example, a reamer head is often removably attached to the shaft 52 employed to rotate the reamer.

The coupling head 54, the most proximal end of the accessory 48, is formed to have three longitudinally spaced apart sections. The first, most proximal section of the coupling head 54 is a boss 302. Boss 302 is dimensioned to closely slip fit in spindle bore 104 and receive the torque output by the spindle 42. In the illustrated versions of the invention, bore 104 has a hexagonal cross sectional profile. Therefore, in this version of the invention, coupling head boss 302 has a hexagonal shape and is dimensioned to be of marginally smaller size than bore 104. The individual outer facial surfaces 303 of boss receive the torque that is transmitted by the complementary adjacent inner faces 105 of spindle 42. The adjacent faces 303 of boss 302 meet at edges 309 (one identified in FIG. 27A). Boss 302 is thus formed so as to have a number of edges 309 that are located circumferentially around the boss.

The second, intermediate section of coupling head 54 is the body 304. Coupling head body 304 is shaped to closely slip fit in spindle bore 120. In the illustrated version of the invention, spindle bore 120 has a circular cross sectional shape. Coupling head body 304 has an identical circular cross section shape with a diameter marginally less than that of spindle bore 120. The coupling head body 304, it is further understood, occupies a cross sectional area greater than that occupied by the coupling head boss 302. Thus, the outer surface of body 304 is understood to be located radially outwardly of the outer perimeter of boss 302. While the coupling head body 304 generally has a constant diameter along its length, the coupling head body 304 is further formed to have a groove 306 that extends circumferentially around and inwardly from the outer surface of the body. Groove 306 is positioned at approximately midway between the proximal and distal ends of the body, and distally forward of a plurality of spaced apart slots 308. More particularly, groove 306 is positioned so that, when the coupling head 54 is seated in the handpiece spindle 42, the proximal surface of the head body 304 that defines the groove is approximately aligned with the proximal interior surfaces of spindle 42 that define spindle slots 114. Groove 306 is partially defined by opposed first and second tapered surfaces (not identified). The first tapered surface, the distal most recessed surface tapers inwardly and proximally rearward from the outer surface of the body. The second tapered surface, the tapered surface located forward of the below described slots 308, tapers inwardly distally forward.

The proximal end of the coupling head body 304 is further formed to define a number of circumferentially spaced apart slots 308. The base of each slot 308 is defined by a flat face 310 that is recessed relative to the surrounding curved outer surface of the rest of the coupling head body 304. As seen in FIG. 27A, face surfaces 310 are located radially outwardly of the faces 303 forming the hexagonal coupling head boss 302. Each slot 308 has a proximal end opening that opens into space immediately adjacent the associated boss face. The proximal end openings into slots 308 are defined by opposed beveled faces 312 integral with body 304. The adjacent abutting beveled faces 312 that define the proximal end openings into adjacent slots 308 meet at an edge 314. Each edge 314 is aligned with a separate one of the boss edges 309.

Shoulder 305 is the most distal section of the coupling head 54. The shoulder 305, which is contiguous with coupling head body 304, has a diameter greater than that of the body so as to have a proximally directed face (not identified) adjacent the distal end of the body 304 that projects radially beyond the outer surface of the body. Cutting accessory 48 is further constructed so that when boss 302 is seated in spindle bore 120, the proximally directed face of shoulder 305 is located immediately adjacent the distally directed face of the spindle 42. In some versions of the invention, especially in coupling heads integral with an attachment 320 (FIG. 32) as described below, shoulder 305 is physically separate from the rest of the coupling head 54. In these versions of the invention, shoulder 305 is press fit over the associated shaft to rotate in unison with the shaft.

Surgical handpiece 20 of this invention is prepared for operation by inserting cutting accessory 48 into the handpiece spindle 42. This process begins by the insertion of the cutting accessory coupling head 54 in spindle bore 120. Eventually points 314 of the coupling head body 304 press against pins 240. The manual force of this action is enough to overcome the opposite force imposed by spring 254. Thus, the continued application of this force results in the pushing of pins 240 diagonally outwardly and rearwardly. Pins 240 thus ride up over the outer surface of the coupling head body 304.

As coupling head 54 is continued to be inserted into the spindle 42, one of the beveled faces 312 of the coupling head body 304 abuts spindle pin 121. The continued insertion of the coupling head 54 results in the rotation of the coupling head until pin 121 seats in the body slot 308 with which the beveled face 312 is adjacent. This rotational movement of the coupling head 54 ensures that, as the coupling head is continued to be inserted into the spindle 42, the coupling head boss 302 is aligned with and seats in the spindle bore 104.

Figure 28:
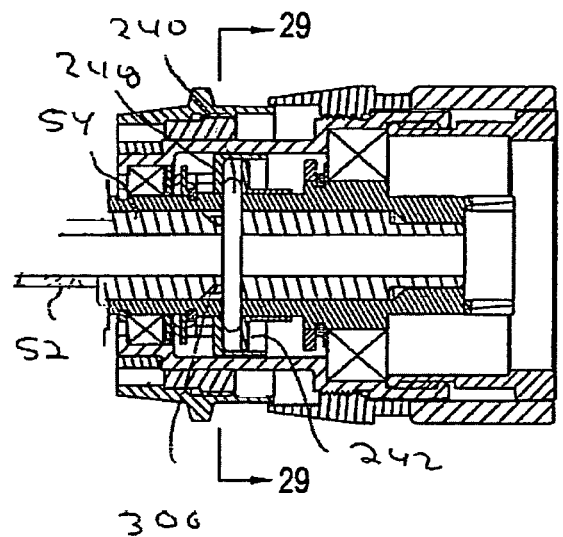
FIG. 28 depicts how a coupling assembly pin seats in a groove of the coupling head according to this invention.
Figure 29:
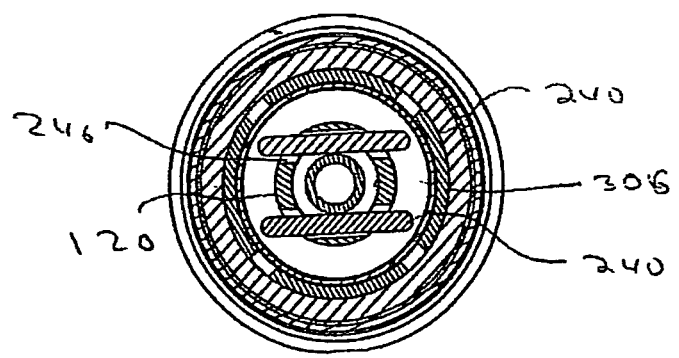
FIG. 29 is a lateral cross section view illustrating how the coupling assembly pins seat in the coupling head indentation.

Once the accessory coupling head 52 is so seated, spring 254 pushes the sub-assembly of pins 240 and washers 242 and 248 forward. This movement results in the pins 240 moving diagonally forward in spindle slots 114, toward the coaxial longitudinal center axes of the accessory coupling head 54 and the spindle bore 120. This results in the seating of pins in coupling head groove 306, as seen in FIGS. 28 and 29. This seating of pins 240 in groove 306 latches coupling head 54 and, therefore, cutting accessory 48, to the handpiece spindle 42.

Clutch 44 is then set to couple the spindle 42 to one of the gear train drive heads 86 or 92 so that the spindle rotates with the selected drive head. Specifically, the clutch 44 is set so that torque pins 184 seat in the notches 88 or 94 of the drive head 86 or 92, respectively, with which the spindle is to be connected. The setting, the longitudinal positioning of, the torque pins 184 is performed by rotating shift ring 202. The rotation of shift ring 202 results in the helical movement of ball bearings 216 in rotary housing slots 148. The longitudinal displacement of ball bearings 216 results in an identical longitudinal displacement of the shifter housing 186. The longitudinal movement of the shifter housing 186 causes a like movement of the inner shifter 180.

Since torque pins 184 are integral with inner shifter 180, longitudinal displacement of the inner shifter results in the selective seating of the pins in either the notches 88 of the proximally located drive head 86 or notches 94 of the distally located drive head 92.

Handpiece 20 of this invention is now ready for operating. The depression of trigger switch 32 results in the actuation of motor 24. Motor shaft 26 rotates. Gear train 36 reduces the rotation moment output by shaft to two different speeds. Specifically, the gears internal to the gear train cause drive head 86 to rotate at a first reduced speed. Drive head 92 is caused to rotate at a second reduced speed less than the first reduced speed.

Depending on the setting of the clutch 44, the torque pins 184 are seated in the notches 88 or 94 of one of the drive heads 86 or 92, respectively. The torque pins 184 thus rotate at the speed of the drive head 86 or 92 with which the pins are engaged. The torque pins 184 extend through the outer coupler slots 134. Consequently, the rotation of the torque pins results in a like movement of the outer coupler 124 and, therefore spindle 42. Since the coupling head boss 302 is relatively closely fitted in the spindle bore 104, and these components have non-circular cross sectional profiles, rotary motion of the spindle 42 is transferred by boss 302 to the coupling head 54 and the rest of the cutting accessory 48.

Figure 30:
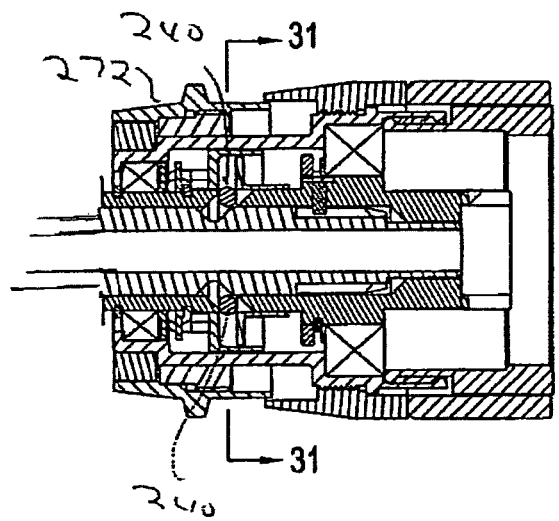
FIG. 30 is a cross sectional view illustrating the position of the coupling assembly when in the load state.
Figure 31:
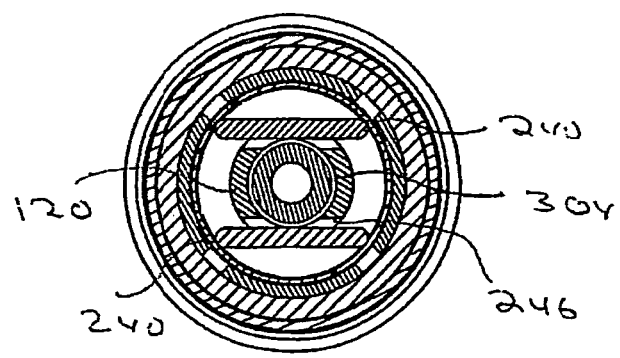
FIG. 31 is a lateral cross section view illustrating the position of the coupling assembly pins when in the load state.

When it is time to remove the cutting accessory 48, actuator sleeve 272 is pushed rearwardly. This movement of the actuator sleeve 272 results in a diagonal rearward and outward movement of pins 240. Pins 240 thus retract out of the coupling head groove 306 and spindle bore 120, as seen in FIGS. 30 and 31. This allows the cutting accessory 48 to be removed and a new accessory to be removably coupled to the handpiece 20.

Clutch 44 of surgical handpiece 20 of this invention is constructed so that torque pins 184 directly transfer the rotational motion output by a drive head 86 or 92 directly to the spindle-outer coupler sub-assembly. Each clutch pin 184 extends laterally through the output coupler 124, which is an extension of spindle 42. Thus, the clutch pins 184 do not occupy a significant amount of longitudinal space. Also, the shifter housing indentations 194 in which ball bearings 216 are spaced relatively close to the clutch pins 184. In some versions of this invention, the distance from the center of the indentions 194 to the center of the clutch pins is 2.0 cm or less. In more preferred versions of this invention this distance is 1.0 cm or less. Collectively, these features of the invention make it possible to provide an inner shifter and shifter housing assembly that has an overall length of 3.0 cm and, more preferably, 2.0 cm or less. In most preferred versions of this invention, the overall length of this sub-assembly is 1.0 cm or less.

Thus, the clutch 44 of this invention is relatively compact in length. This makes it possible to provide a handpiece with gear train and clutch assembly that likewise has a reduced axial length. Moreover, employing the clutch 44 of this invention reduces the extent to which the mass of components forming the handpiece 20 are distributed away from the center of gravity. By centering the component mass near the center line of the center of gravity, the stress to which a surgeon is exposed when precisely positioning the handpiece 20 is reduced.

When an attachment/cutting accessory coupling head is fitted to the spindle 42 of the handpiece of this invention, there is a relatively long and close interface between the inner wall of the spindle 42 that defines bore 120 and the outer surface of the coupling head body 304. In some versions of this invention, this interface has a length of 0.6 inches or more. In more preferred versions of the invention, this interface has a length of 1.0 inches or more. This interface is located distal to where the spindle transfer torque to the coupling head boss 302. This construction minimizes the wobble of the coupling head in the spindle when both components are rotated. The minimization of the coupling head wobble results in a like reduction of the wobble present at the cutting accessory tissue working head 50.

Moreover, when coupling head 54 is fitted in spindle bore 120, the coupling head shoulder 305 abuts the distal end opening of the spindle that defines the bore. Thus collectively, pins 240 and shoulder 305 prevent longitudinal wobble of the coupling head 54 in the spindle. Since the distal end of the rotating spindle 120 is spaced slightly forward of the static components of the handpiece 20, the presence of shoulder 305 does not inhibit rotation of the cutting accessory 48. To further ensure that there is no contact between the shoulder 305 and the static components of the handpiece 20, the shoulder is dimensioned so it does not subtend area subtended by the static components. Thus, the outer diameter of shoulder 305 is less than the distal end opening into the rotary housing defined by lip 162.

Figure 32:
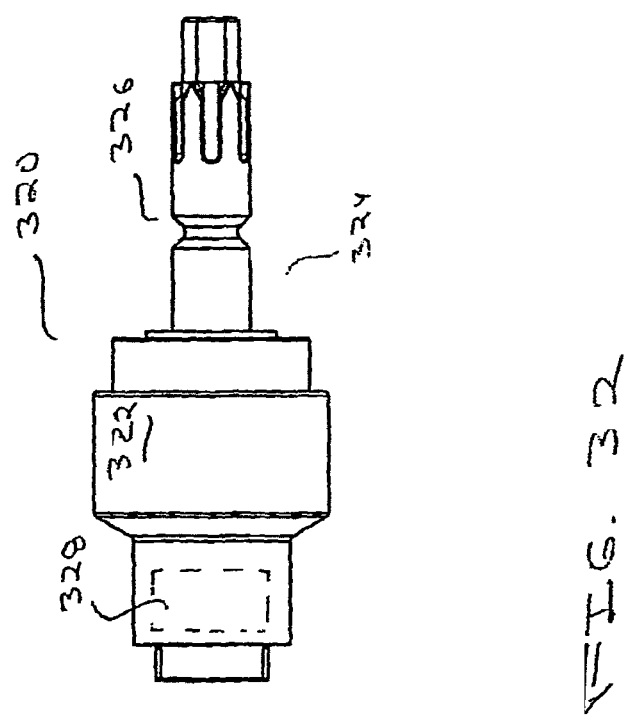
FIG. 32 is a plan view of an attachment with the coupling head of this invention.

FIG. 32 illustrates an attachment 320 constructed in accordance with this invention. Attachment 320 includes a housing 322. An input shaft 324 is extends rearwardly from the housing 322. Input shaft is shaped to have a proximal end coupling head 326 with the same features as cutting accessory coupling head 54. Internal to the housing is a coupling assembly 328 represented by a phantom rectangle. Coupling assembly 328 is designed to releasably hold the proximal end of a cutting accessory (not illustrated) for rotation. The exact structure of the coupling assembly 328 is not relevant to this invention. Coupling assembly 328 may include the features of coupling assembly 46. Alternatively, coupling assembly 328 may be provided with features to hold coupling heads other than the described coupling head 54 for rotation. These include coupling heads with trinkle fittings, Hudson® fittings and modified trinkle fittings that are known in the surgical art.

Input shaft 324 rotates coupling assembly 328. In some versions of the invention, input shaft 324 and the spindle of coupling assembly 328 are the same component. In these versions of the invention, attachment 320 thus serves as a means for connecting an accessory with a head different from coupling head 54 to the handpiece. In these versions of the invention, the attachment rotates at the speed at which the handpiece spindle 42 rotates. In other versions of the invention, there is a speed reducer or speed increaser gear assembly internal to the attachment housing 322 for transferring the rotational moment received by the input shaft 326 to the coupling head. The Applicants' Assignee's U.S. Pat. No. 5,993,454, DRILL ATTACHMENT FOR A SURGICAL DRILL, issued 30 Nov. 1999 and incorporated herein by reference, shows one such assembly. This type of attachment may be provided with a spindle and coupling assembly substantially identical to the spindle 42 and coupling assembly 46 of this invention.

The foregoing is directed to one specific version of the invention. It should be appreciated that alternative versions of the handpiece, cutting accessory and attachment of this invention may have features different from what have been described.

For example, there is no requirement that all handpieces of this invention include both the described clutch and coupling assembly. Some versions of the invention may have only the clutch or only the coupling assembly.

The gear train and drive heads of this invention may be of different design. For example, in some versions of the invention, the gear train may have three or more drive heads, each or which, in response to the single input rotational moment, operates at a different rotational speed. In some versions of the invention, the gear train has gears that cause one or more drive heads to rotate at speeds faster than those at which the motor shaft 26 rotates.

The means by which the motor 22 rotates shaft 26 may likewise vary from what has been described.

Similarly, the structure of the clutch 44 may differ from what has been described. For instance, some versions of the invention may have few or more laterally extending members, clutch pins or other torque transmitting components, for simultaneously engaging a gear train drive head 86 or 92 and the spindle 42. In some versions of the invention, clutch 44 may even include a single one of these members.

In some versions of the invention, the inner shifter and/or outer shifter may be arranged so that the points at which longitudinal motion are transferred to this sub assembly (indentions 194 in the described embodiment) are within the longitudinal slice in which the lateral member that transfers torque from one of the drive heads to the spindle is located. Such construction can further reduce the overall longitudinal length of the clutch.

Also in some versions of the invention, the clutch pins may be integrally attached to the spindle. In these versions of the invention, the spindle itself is displaced in order to cause the clutch pins to engage the appropriate gear train drive head.

Similarly, in other versions of the invention, means other than a rotating shift ring may be employed to set the position of the clutch pins. In some versions of the invention, a switch member moveable mounted to the handpiece housing to move longitudinally is the surgeon-actuated component that is displaced to set the position of the clutch pins.

Figure 33:
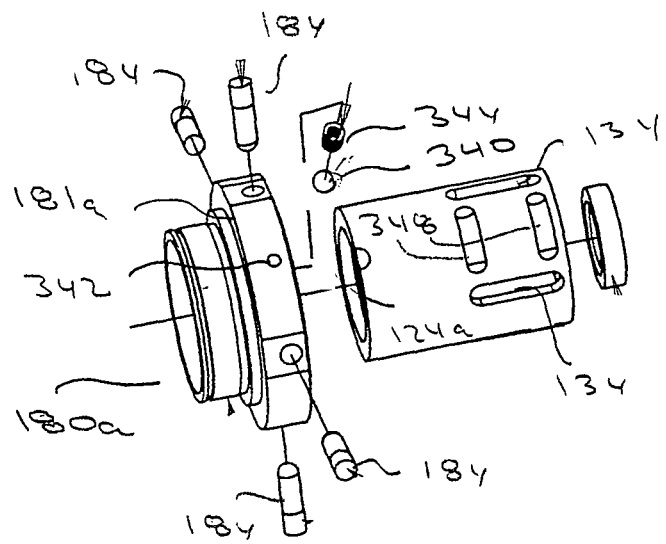
FIG. 33 is an exploded view of a section of an alternative clutch assembly of this invention.
Figure 34:
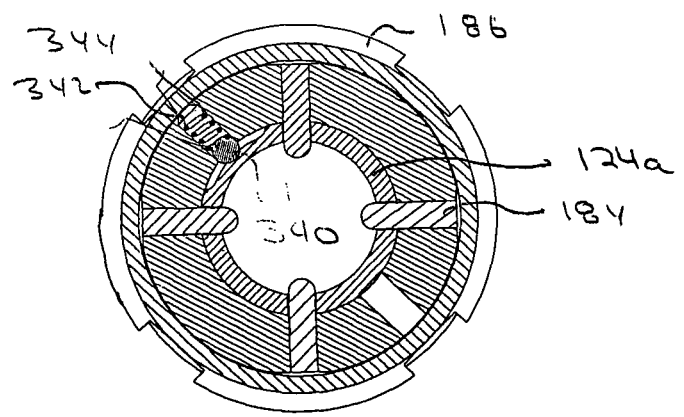
FIG. 34 is a cross sectional view of a portion of the assembly of FIG. 33.

As seen in FIGS. 33 and 34, it is possible to provide the clutch assembly of this with a tactile and audible feedback assembly for indicating the switching of the clutch between the clutch states. In the illustrated feedback assembly, the feedback is provided by a detent ball 340. Detent ball 340 is seated in a bore 342 formed in the base 181*a* of inner shifter 180*a*. The detent ball is positioned to extend inwardly, towards the outer coupler 124*a*. A spring 344 is also seated on inner shifter bore 342 so as to urge ball 340 inwardly, toward the outer coupler 124. Shifter housing 186, it is understood, is disposed over the inner shifter 180*a*. Thus, the inner annular wall of the shifter housing 186 functions as the static surface against which the outer end of spring 344 abuts.

Figure 8:
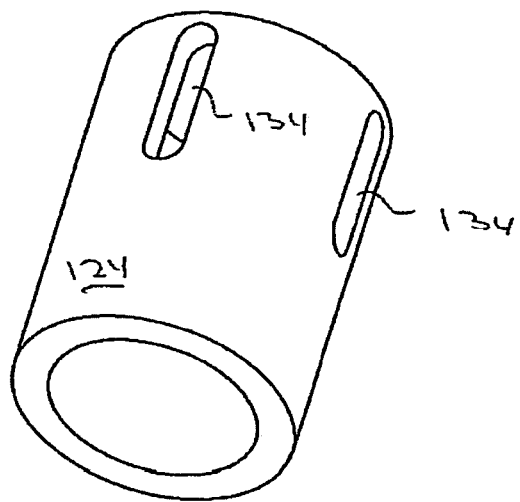
FIG. 8 is a perspective view of the output coupler.
Figure 9:
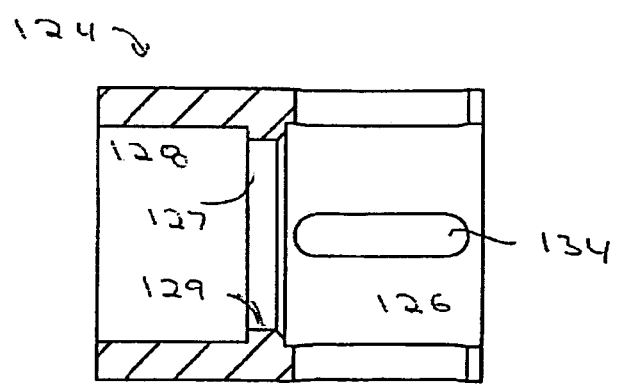
FIG. 9 is a cross sectional view of the output coupler.

The outer coupler 124*a* has the same basic geometry of the first described outer coupler 124 (FIGS. 8 and 9). Outer coupler 124*a* is also formed to have two parallel arcuately extend grooves 348. Grooves 348 are formed in the outer surface of the outer coupler 124*a* between two adjacent slots 134 formed in the coupler. A first one of the grooves 348 is located adjacent the distal ends of the slots 134. The second groove is located adjacent the proximal end of the slots 134.

As the clutch is actuated, inner shifter base 181*a* moves between the opposed ends of the outer coupler slots 134. This movement of the inner shifter causes detent ball 340 to move out of a first one of the grooves 348 into the second groove 348. The spring resistance overcomes moving the ball 340 out of the first groove 348 provides an initial tactile feedback that the clutch is being moved from a first state. When the inner shifter base 181*a* is moved to the position wherein the clutch pins 184 engage the second one of the drive heads 86 or 92, the detent ball 340 seats in the groove 348 aligned with the drive head. This results in an audible mechanical. Also, the individual actuating the shift ring 202 (FIG. 1) is exposed to an additional resistance when try urge the ball out of the groove.

Thus, the feedback assembly of the clutch of this version of the invention provides feedback both when the clutch is moved from the first setting and when the clutch sets in the second setting.

Also, the structure of the coupling assembly 46 and complementary attachment/cutting accessory coupling head may vary from what has been described. There is no requirement that in all versions of the invention the surfaces of the spindle that output torque and complementary coupling head boss 302 have a hexagonal or even a polygonal cross sectional profile. It is believed that a polygonal cross sectional geometry is the most efficient for ensuring torque transfer to the coupling head.

Similarly, the coupling head body 304 may have a geometry different from what has been described and illustrated. There is no requirement that in all versions of the invention this component and the complementary spindle bore have circular cross-sectional profiles. In some versions of the invention, these components may even have one or more planar faces. It is believed though such geometry is an optimal geometry for reducing coupling head wobble. Similarly, there is no requirement that in all versions of the invention, the indentation defined by the coupling head body for receiving the locking member associated with the handpiece coupling assembly be an annular groove. In some versions of the invention, one or more indentations are provided in the coupling head body for receiving the complementary locking member integral with the complementary handpiece coupling assembly.

In some versions of the invention, the coupling body may not have any geometric features for receiving a complementary coupling assembly locking members. Also, there may be versions of the invention wherein the geometric features for facilitating the engagement of the handpiece coupling assembly with the coupling head project beyond the surface of the coupling head body.

Similarly, there may be versions of the invention in which the coupling head body has a diameter that is identical with that of the distally adjacent attachment/accessory shaft. In still other versions of the invention, the attachment/accessory shaft may have a diameter greater than that of the coupling head.

Likewise, an accessory/attachment coupling head of this invention may be constructed with geometric features different from slots 308 and beveled faces 312 to facilitate the alignment of the coupling head in the spindle bore. Some versions of the invention may not even be provided with any of these features.

Other coupling assemblies may, instead of holding an attachment/accessory coupling head to the spindle serve only to cause the coupling head to be driven by the spindle.

Therefore, it is an object of the appended claims to cover all such variations and modifications that come within the true spirit and scope of the invention.

What is claimed is:

1. A cutting accessory for performing a medical/surgical procedure, said cutting accessory comprising:
 a drive shaft having opposed proximal and distal ends;
 a tissue working member attached to or integral with the distal end of said drive shaft; and
 a coupling head attached to the proximal end of said drive shaft, said coupling head having:
  a boss having a plurality of planar faces that are located circumferentially around said boss, each face having a width thereacross, each face being in a plane that is angled relative to the planes of adjacent faces and wherein each pair of adjacent faces meet to define an edge so that said boss has a plurality of angularly spaced apart edges that are located circumferentially around said boss;
  a body located distally forward of said boss, said body having:
   an outer surface with a circular cross sectional profile and a diameter such that said body extends radially outwardly beyond said boss;
   opposed proximal and distal ends, the proximal end being located adjacent said boss;
   a plurality of spaced apart slots that extend inwardly from the outer surface of said body, each said slot extending distally forward from the proximal end of said body, wherein each said slot is aligned with a separate one of the boss faces, has a width thereacross less than the width across the aligned boss face and has a proximal end opening that opens into space immediately adjacent the boss face with which said slot is aligned, the proximal end opening being defined by a pair of opposed beveled faces of the body that taper inwardly towards each other, wherein, adjacent beveled faces that define adjacent slots in the body meet at an edge, each edge present where adjacent body beveled faces meet being aligned with a separate one of the edges where an adjacent pair of boss faces meet; and
   at least one indentation that extends inwardly from the body outer surface, the at least one indentation being located distally forward of the slots; and
  a shoulder located distally forward of said coupling head body so as to be spaced distally forward from the at least one indentation in said coupling head body, said shoulder extending radially beyond the outer surface of said coupling head body so as to have a proximally directed face that projects radially beyond said coupling head body.

2. The cutting accessory of claim 1, wherein, the at least one indentation of said coupling head body is at least partially defined by a recessed surface that tapers inwardly and distally forward from the body outer surface.

3. The cutting accessory of claim 1, wherein, said at least one indentation is a single annular groove that extends circumferentially inwardly from and around the outer surface of the coupling head body.

4. The cutting accessory of claim 1, wherein said coupling head body is formed so that the outer surface of the body has a constant diameter along the length of said body.

5. The cutting accessory of claim 1, wherein, said coupling head body is formed so that each slot has a base that is defined by a face surface of said body that is located inward of the outer surface of the body, each slot-defining face surface being parallel and distal to the adjacent boss face.

6. The cutting accessory of claim 1, wherein, said coupling head shoulder has a diameter greater than that of said drive shaft.

7. The cutting accessory of claim 1, wherein said coupling head body is further formed so that the beveled faces are planar.

8. The cutting accessory of claim 1, wherein said tissue working member is a reamer head.

9. A cutting accessory for performing a medical/surgical procedure, said cutting accessory comprising:
 a drive shaft having opposed proximal and distal ends;

a tissue working member attached to or integral with the distal end of said drive shaft; and a coupling head attached to the proximal end of said drive shaft, said coupling head having:

a boss having a plurality of planar faces that are located circumferentially around said boss wherein: each face is in a plane that is angled relative to the planes of adjacent faces; each face has a width thereacross; and each pair of adjacent faces meets at an edge so that the boss has a plurality of angularly spaced apart edges that are located circumferentially around said boss;

a body located distally forward of said boss, said body having:

an outer surface with a circular cross sectional profile and a diameter such that said body extends radially outwardly beyond said boss;

opposed proximal and distal ends, the proximal end being located adjacent the faces of said boss;

a plurality of spaced apart slots, each said slot extending distally forward from the proximal end of said body, wherein each slot has: a base that is defined by a recessed planar face in the body, each slot base-defining face being parallel to a separate one of the faces of said boss; a width less than the width of the boss face with which the slot is aligned; and each said slot has a proximal end opening that opens into space immediately adjacent the boss face with which the slot is aligned, the proximal end opening defined by a pair of opposed beveled faces of said body, the beveled faces taper inwardly towards each other wherein adjacent beveled faces that define adjacent slots in the body meet an edge, wherein each edge defined by the adjacent beveled faces of said coupling head body is aligned with a separate one of the boss edges; and a groove that extends inwardly from the body outer surface and circumferentially around the body outer surface, the groove being located distally forward of the slots; and a shoulder located distally forward of said coupling head body so as to be spaced distally forward from the groove in the coupling head body, said shoulder extending radially beyond the outer surface of said body so as to have a proximally directed face that projects radially beyond said body.

10. The cutting accessory of claim 9, wherein, said coupling head body is further formed so that the groove in said coupling head body is at least partially defined by a recessed surface that tapers inwardly and distally forward from the body outer surface.

11. The cutting accessory of claim 9, wherein said coupling head body is further formed so that the groove in the body is defined by first and second opposed recessed surfaces that extend inwardly from the outer surface of said body, the first recessed surface being a tapered surface that extends inwardly and distally forward and the second recessed surface being a tapered surface that extends inwardly and proximally rearward towards the first tapered surface.

12. The cutting accessory of claim 9, wherein said tissue working member is a reamer head.

13. The cutting accessory of claim 9, wherein said coupling head body is further formed so that the beveled faces are planar.

14. The cutting accessory of claim 9, wherein, said coupling head body is formed so that, with the exception of the groove, the outer surface has a constant diameter along the length of said body.

15. A cutting accessory for performing a medical/surgical procedure, said cutting accessory comprising:

a boss that forms the proximal most portion of said cutting accessory, said boss having a plurality of planar faces that are located circumferentially around said boss wherein: each face is in a plane that is angled relative to the planes of the adjacent faces; each face has a width thereacross;

and each pair of adjacent faces meet to define an edge so that the boss has a plurality of angularly spaced apart edges that are located circumferentially around said boss;

a body located distally forward of said boss, said body having:

an outer surface with a circular cross sectional profile and a diameter such that said body extends radially outwardly beyond said boss;

opposed proximal and distal ends, the proximal end being located adjacent the faces of said boss; and a plurality of spaced apart slots that extend inwardly from the outer surface of said body, each said slot extending distally forward from the proximal end of said body, wherein each said slot is aligned with a separate one of the boss faces, has a width that is less than the width across the aligned boss face and has a proximal end opening that opens into space immediately adjacent the boss face with which said slot is aligned wherein, each slot proximal end opening is defined by a pair of opposed beveled faces that taper inwardly towards each other, wherein adjacent beveled faces that define the proximal end openings into adjacent slots in said body meet to define an edge so that said body has a plurality of angularly spaced apart edges and is further shaped so that the edge defined by a pair of adjacent beveled faces is aligned with a separate one of the boss edges;

at least one indentation that extends inwardly from the outer surface of said body, the at least one indentation being located distally forward of the slots and being at least partially defined by a recessed surface that tapers inwardly and distally forwardly from the body outer surface;

a shoulder located distally forward of said body and spaced distally forward from the at least one indentation of said body, said shoulder extending radially beyond the outer surface of said body so as to have a proximally directed face that projects radially beyond said body;

a drive shaft that extends distally forward from said shoulder that has a distal end that is spaced from said shoulder; and a tissue working member attached to or integral with the distal end of said drive shaft.

16. The cutting accessory of claim 15, wherein, said at least one indentation of said body is an annular groove that extends inwardly around the body outer surface.

17. The cutting accessory of claim 15, wherein, said body is shaped so that, with the exception of the at least one indentation, the outer surface has a constant diameter along the length of said body.

18. The cutting accessory of claim 15, wherein the number of faces formed on said boss and the number of slots formed in said body are identical.

19. The cutting accessory of claim 15, wherein said tissue working member is a reamer head.

20. The cutting accessory of claim 15, wherein said body is further formed so that the beveled faces are planar.

* * * * *